United States Patent
Newton et al.

(10) Patent No.: US 10,201,501 B2
(45) Date of Patent: Feb. 12, 2019

(54) MIXED METAL COMPOUNDS USED AS ANTACIDS

(75) Inventors: Maurice Sydney Newton, Sandbacj (GB); James David Morrison, Norwich (GB); Ruth Diane Pennel, Wirral (GB); Nigel Peter Rhodes, Warrington (GB); Alexis John Toft, Warrington (GB)

(73) Assignee: OPKO IRELAND GLOBAL HOLDINGS, LTD., Grand Cayman (KY)

( * ) Notice: Subject to any disclaimer, the term of this patent is extended or adjusted under 35 U.S.C. 154(b) by 839 days.

(21) Appl. No.: 12/670,834

(22) PCT Filed: Jul. 24, 2008

(86) PCT No.: PCT/GB2008/002533
§ 371 (c)(1),
(2), (4) Date: Jan. 26, 2010

(87) PCT Pub. No.: WO2009/016349
PCT Pub. Date: Feb. 5, 2009

(65) Prior Publication Data
US 2010/0203152 A1    Aug. 12, 2010

(30) Foreign Application Priority Data
Jul. 27, 2007 (GB) .................................. 0714670.7

(51) Int. Cl.
| | | |
|---|---|---|
| A61K 9/20 | (2006.01) | |
| A61K 9/28 | (2006.01) | |
| A61K 33/10 | (2006.01) | |
| A61K 33/26 | (2006.01) | |
| A61K 45/06 | (2006.01) | |

(52) U.S. Cl.
CPC .......... *A61K 9/2027* (2013.01); *A61K 9/2059* (2013.01); *A61K 9/2846* (2013.01); *A61K 33/10* (2013.01); *A61K 33/26* (2013.01); *A61K 45/06* (2013.01)

(58) Field of Classification Search
None
See application file for complete search history.

(56) References Cited

U.S. PATENT DOCUMENTS

| | | |
|---|---|---|
| 2,222,924 A | 11/1940 | Weiss |
| 2,812,344 A | 11/1957 | Oroshnik |
| 3,101,270 A | 8/1963 | Evans et al. |
| 3,395,211 A | 7/1968 | Wielich |
| 3,650,704 A * | 3/1972 | Kumura et al. ........... 423/415.1 |
| 3,743,098 A | 7/1973 | Martinez |
| 3,796,792 A | 3/1974 | Miyata et al. |
| 3,879,523 A | 4/1975 | Miyata et al. |
| 3,984,392 A | 10/1976 | van der Veen et al. |
| 4,192,900 A | 3/1980 | Cheng |
| 4,254,099 A | 3/1981 | Asmussen et al. |
| 4,351,814 A | 9/1982 | Miyata et al. |
| 4,370,280 A | 1/1983 | Oediger et al. |
| 4,415,555 A | 11/1983 | Anabuki et al. |
| 4,458,026 A | 7/1984 | Reichle |
| 4,514,389 A * | 4/1985 | Miyata .......................... 424/601 |
| 4,566,986 A | 1/1986 | Waldmann |
| 4,582,705 A | 4/1986 | Primes et al. |
| 4,609,543 A | 9/1986 | Morris et al. |
| 4,629,626 A | 12/1986 | Miyata et al. |
| 4,661,330 A | 4/1987 | Chane-Ching et al. |
| 4,689,219 A | 8/1987 | Sugden |
| 4,735,629 A | 4/1988 | Glemser et al. |
| 4,786,510 A | 11/1988 | Nakel et al. |
| 4,801,454 A | 1/1989 | Coveney |
| 4,970,079 A | 11/1990 | Hem et al. |
| 4,994,283 A | 2/1991 | Mehansho et al. |
| 5,002,747 A | 3/1991 | Le Loarer |
| 5,085,869 A | 2/1992 | Olthoff et al. |
| 5,112,604 A | 5/1992 | Beaurline et al. |
| 5,153,156 A | 10/1992 | Schutz et al. |
| 5,173,284 A | 12/1992 | Moisset et al. |
| 5,185,093 A | 2/1993 | Ichikawa et al. |
| 5,213,794 A | 5/1993 | Fritsch et al. |
| 5,246,899 A | 9/1993 | Bhattacharyya |
| 5,273,767 A | 12/1993 | Burgum |
| 5,300,302 A | 4/1994 | Tachon et al. |
| 5,506,248 A | 4/1996 | Nikfar et al. |

(Continued)

FOREIGN PATENT DOCUMENTS

| | | |
|---|---|---|
| CA | 1198674 A | 5/1985 |
| DE | 2061136 A1 | 7/1971 |

(Continued)

OTHER PUBLICATIONS

EVONIK® product information for Eudragite E 100, Eudragite E PO and Eudragite E 12,5, Oct. 2011, pp. 1-6.*

(Continued)

*Primary Examiner* — David J Blanchard
*Assistant Examiner* — Ivan A Greene
(74) *Attorney, Agent, or Firm* — Marshall, Gerstein & Borun LLP

(57) ABSTRACT

There is provided use of a mixed metal compound in the manufacture of medicament for neutralizing or buffering stomach acid, wherein the mixed metal compound contains at least one trivalent metal selected from iron (III) and aluminum and at least one divalent metal selected from of magnesium, iron, zinc, calcium, lanthanum and cerium, wherein (A) the mixed metal compound is of formula (I): $M^{II}_{1-a}M^{III}_{a}O_{b}A^{n-}_{c}\cdot zH_2O$ (I) where $M^{II}$ is the at least one bivalent metal; $M^{III}$ is the at least one trivalent metal; $A^{n-}$ at least one n-valent anion; $2+a=2b+\Sigma cn$ and $\Sigma cn<0.9a$, and z is 2 or less, and/or (B) the mixed metal compound is provided in the form of a granular material comprising (i) at least 50% by weight, based on the weight of the granular material, of the mixed metal compound (ii) from 3 to 12% by weight, based on the weight of the granular material, of non-chemically bound water, and (iii) no greater than 47% by weight based on the weight of the granular material of excipient.

39 Claims, 1 Drawing Sheet

(56) References Cited

U.S. PATENT DOCUMENTS

| | | |
|---|---|---|
| 5,514,281 A | 5/1996 | Boos et al. |
| 5,525,305 A | 6/1996 | Mineku et al. |
| 5,571,336 A | 11/1996 | Wurzburger et al. |
| 5,651,997 A | 7/1997 | Makino et al. |
| 5,654,011 A | 8/1997 | Jackson et al. |
| 5,656,080 A | 8/1997 | Staniforth et al. |
| 5,817,340 A | 10/1998 | Roche et al. |
| 5,846,426 A | 12/1998 | Boos et al. |
| 5,968,976 A | 10/1999 | Murrer et al. |
| 6,028,023 A | 2/2000 | Vierheilig |
| 6,039,981 A | 3/2000 | Woo et al. |
| 6,103,126 A | 8/2000 | Boos et al. |
| 6,174,442 B1 | 1/2001 | Geisser et al. |
| 6,287,596 B1 | 9/2001 | Murakami et al. |
| 6,448,323 B1 | 9/2002 | Jordan et al. |
| 6,576,255 B1 | 6/2003 | Petereit et al. |
| 6,576,665 B2 | 6/2003 | Dennett, Jr. et al. |
| 6,596,311 B1 | 7/2003 | Dobetti |
| 6,696,087 B2 | 2/2004 | Matsuda et al. |
| 6,720,005 B1 | 4/2004 | Ayres |
| 6,733,780 B1 | 5/2004 | Tyler et al. |
| 6,749,864 B2 | 6/2004 | Makino et al. |
| 6,790,895 B2 | 9/2004 | Stelandre et al. |
| 6,794,367 B1 | 9/2004 | Tanida et al. |
| 6,926,912 B1 | 8/2005 | Roberts et al. |
| 7,259,192 B2 | 8/2007 | Liu et al. |
| 7,300,670 B2 | 11/2007 | Venus et al. |
| 7,799,351 B2 | 9/2010 | Roberts et al. |
| 2002/0122786 A1 | 9/2002 | Matsuda et al. |
| 2003/0150249 A1 | 8/2003 | Gillman et al. |
| 2003/0185886 A1 | 10/2003 | Lee et al. |
| 2004/0022872 A1 | 2/2004 | Sofue et al. |
| 2004/0105896 A1 | 6/2004 | Roberts et al. |
| 2004/0247696 A1 | 12/2004 | Antelman |
| 2005/0260271 A1 | 11/2005 | Bringley |
| 2005/0266071 A1* | 12/2005 | Olmstead ............. A61K 9/0056 424/451 |
| 2006/0177415 A1 | 8/2006 | Burke |
| 2008/0187602 A1 | 8/2008 | Ferdinando et al. |
| 2009/0175959 A1* | 7/2009 | Bando ..................... A61K 9/16 424/683 |
| 2009/0317459 A1 | 12/2009 | Pennel et al. |
| 2010/0215770 A1 | 8/2010 | Newton et al. |
| 2011/0014301 A1 | 1/2011 | Roberts et al. |
| 2012/0093943 A1 | 4/2012 | Newton et al. |
| 2012/0201864 A1 | 8/2012 | Applewhite et al. |
| 2013/0323325 A1 | 12/2013 | Applewhite et al. |

FOREIGN PATENT DOCUMENTS

| | | |
|---|---|---|
| DE | 3346943 A | 7/1985 |
| DE | 3402878 A1 | 8/1985 |
| DE | 3801382 A1 | 8/1989 |
| EP | 0050792 A1 | 5/1982 |
| EP | 0 134 936 A1 * | 3/1985 |
| EP | 0134 936 A1 * | 3/1985 |
| EP | 0134936 A1 * | 3/1985 |
| EP | 0146410 A2 | 6/1985 |
| EP | 0150792 A2 | 8/1985 |
| EP | 0368420 A2 | 5/1990 |
| EP | 0577294 A2 | 1/1994 |
| EP | 0 638 313 A1 | 2/1995 |
| EP | 1304104 A2 | 4/2003 |
| EP | 1413197 A2 | 4/2004 |
| EP | 1707178 A1 | 10/2006 |
| EP | 1932808 A1 | 6/2008 |
| EP | 1946750 A1 | 7/2008 |
| ES | 2018952 A | 5/1991 |
| FR | 1214473 A | 4/1960 |
| FR | 2254556 A1 | 7/1975 |
| GB | 1336866 A | 11/1973 |
| GB | 1378830 A | 12/1974 |
| GB | 2031395 A | 4/1980 |
| GB | 2254556 A | 10/1992 |
| HU | 173556 B | 6/1979 |
| HU | 201880 B | 1/1991 |
| IE | 63343 B1 | 4/1995 |
| IN | 192168 A1 | 3/2004 |
| IN | 192168 | 3/2006 |
| JP | 10-101569 | 1/1900 |
| JP | 61036222 A | 2/1986 |
| JP | 62145024 A | 6/1987 |
| JP | 05155776 A | 6/1993 |
| JP | 05208816 A | 8/1993 |
| JP | 0638313 A | 2/1995 |
| JP | 10059842 A | 3/1998 |
| JP | H10-101569 * | 4/1998 |
| JP | J H10-101569 * | 4/1998 |
| JP | 10236960 A | 9/1998 |
| JP | 3001114 B2 | 1/2000 |
| JP | 2000086537 A | 3/2000 |
| JP | 2001517633 A | 10/2001 |
| JP | 2004089760 A | 3/2004 |
| PL | 189716 B1 | 6/1997 |
| PL | 200957 B1 | 11/1999 |
| SU | 414849 A1 | 9/1977 |
| WO | WO-91/18835 A1 | 12/1991 |
| WO | WO-92/01458 A1 | 2/1992 |
| WO | WO-93/22237 A1 | 11/1993 |
| WO | WO-94/09798 A1 | 5/1994 |
| WO | WO-95/11033 A1 | 4/1995 |
| WO | WO-95/29679 A1 | 11/1995 |
| WO | WO-96/30029 A1 | 10/1996 |
| WO | WO-97/11166 A1 | 3/1997 |
| WO | WO-97/22266 A1 | 6/1997 |
| WO | WO-97/48380 A1 | 12/1997 |
| WO | 9915189 | 4/1999 |
| WO | WO-99/44580 A1 | 9/1999 |
| WO | WO-0032189 A1 | 6/2000 |
| WO | WO-01/27069 A1 | 4/2001 |
| WO | WO-01/49301 A1 | 7/2001 |
| WO | WO-01/049301 A1 | 7/2001 |
| WO | WO-03/013473 A1 | 2/2003 |
| WO | WO-03/017980 A1 | 3/2003 |
| WO | WO-03/028706 A1 | 4/2003 |
| WO | WO-03/072084 A1 | 9/2003 |
| WO | WO-03/092658 A1 | 11/2003 |
| WO | WO-2004/016553 A2 | 2/2004 |
| WO | WO-2004/018094 A1 | 3/2004 |
| WO | 2005012194 A | 2/2005 |
| WO | WO-2005/009381 A2 | 2/2005 |
| WO | WO-2005/012194 A1 | 2/2005 |
| WO | WO-2005/018651 A1 | 3/2005 |
| WO | WO-2005/027876 A1 | 3/2005 |
| WO | 2006085079 A | 8/2006 |
| WO | WO 2006085079 A2 * | 8/2006 |
| WO | WO 2007074909 A1 * | 5/2007 |
| WO | WO 2007074909 A1 * | 7/2007 |
| WO | 2007088343 | 8/2007 |
| WO | WO-2007/135362 A2 | 11/2007 |
| WO | WO-2008/071747 A1 | 6/2008 |
| WO | WO-2008/129034 A1 | 10/2008 |
| WO | WO-2009/016349 A1 | 2/2009 |
| WO | WO-2009/050468 A1 | 4/2009 |

OTHER PUBLICATIONS

Kostura B. et al. ("Rehydration of calcined Mg—Al hydrotalcite in acidified chloride-containing aqueous solution,", Collection of Czechoslovak Chemical Communications, 2007, vol. 72, No. 9, p. 1284-1294. XP002508564.*

Hibino et al.; "Calcination and rehydration behavior of Mg—Fe—C03 hydrotalcite-like compounds," J. Materials Sci. Lett., 19(16):1403-1405 (2000).*

Hollander, Daniel and Harlan, John; "Antacids vs Placebos in Peptic Ulcer Therapy: A Controlled Double-Blind Investigation," 1973, American Medical Association; Journal of the American Medical Association, vol. 226, No. 10, pp. 1181-1185.*

Bejoy, N.; "Hydrotalcite: The Clay that Cures," 2001, Springer; Resonance, vol. 6, No. 2, pp. 57-61.*

(56) References Cited

OTHER PUBLICATIONS

Hudson, Michael J. et al.; "Thermal Conversion of a Layered (Mg/Al) Double Hydroxide to the Oxide," 1995, RSC; Journal of Materials Chemistry, vol. 5, Issue 2, pp. 323-329.*
Ansel, Howard C. et al.; "Pharmaceutical Dosage Forms and Drug Delivery Systems," 1999, Lippincott Williams & Wilkins; Chapters 1-8, pp. 1-243.*
Zhao Y et al., Preparation of layered double-hydroxide nanomaterials with a uniform crystallite size using a new method involving separate nucleation and aging steps, Chemistry of Materials, 2002, vol. 14, No. 10, p. 4286-4291.
Hidetoshi Hirahara; Sawai, Yoshiyuki; Aisawa, Sumio; Takahashi, Satoshi; Umetsu, Yoshio; Narita, Eiichi. Department of Chemical Engineering, Faculty of Engineering, Iwate University, Morioka, Japan. Synthesis and antacid property of Mg—Fe layered double hydroxide. Journal of the Clay Science Society of Japan—Nendo Kagaku (2002), 42(2), 70-76.
Miederer, S.-E.; Wirtz, M.; Fladung, B. Department of Internal Medicine, Gastroenterology and Metabolism, University of Bonn, University of Bielefeld, Leverkusen, Germany. Acid neutralization and bile acid binding capacity of hydrotalcite compared with other antacids: an in vitro study. Chinese Journal of Digestive Diseases (2003), 4(3), 140-146.
Grubel, P.; Bhaskar, K. R.; Cave, D. R.; Garik, P.; Stanley, H. E.; Lamont, J. T. Division of Gastroenterology, St. Elizabeth's Medical Center of Boston, Harvard Medical School, Boston University, Boston, MA, USA. Interaction of an aluminum-magnesium-containing antacid and gastric mucus: possible contribution to the cytoprotective function of antacids. Alimentary Pharmacology and Therapeutics (1997), 11(1), 139-145.
Vatier, J.; Ramdani, A.; Vitre, M. T.; Mignon, M. Cent. Hospitalier Univ. X. Bichat, Paris, Fr. Antacid activity of calcium carbonate and hydrotalcite tablets: Comparison between in vitro evaluation using the "artificial stomach-duodenum" model and in vivo pH-metry in healthy volunteers. Arzneimittel-Forschung (1994), 44(4), 514-18.
Playle A.C., Gunning S,R, and Llewellyn. The in vitro antacid and anti-pepsin activity of hydrotalcite. Pharm. Acta Helv. 49, Nr.9/10 (1974) p. 298-302.
MacCara M.E. et al., Acid neutralization capacity of Canadian antacid formulations, Can. Med. Assoc. J., Mar. 1, 1985, vol. 132, p. 523-527.
Zhu H et al., "Different Mg to Fe ratios in the mixed metal MgFe hydroxy-carbonate compounds and the effect on phosphate binders." Journal of Pharmaceutical Sciences, Jan. 2002, vol. 91, No. 1, Jan. 2002 pp. 53-66, XP002497447 ISSN: 0022-3549.
Abramowitz et al., Serum alkaline phosphatase and phosphate and risk of mortality and hospitalization, Clin. J. Am. Soc. Nephrol., 1:1064-71 (2010).
Adachi-Pagano et al., Synthesis of Al-rich hydrotalcite-like compounds by using the urea hydrolysis reaction-control of size and morphology, J. Mater. Chem., 13(8):1988-93 (2003).
Albaaj et al., Hyperphosphataemia in renal failure: causes, consequences and current management, Drugs, 63(6):577-96 (2003).
Ambrogi et al., Intercalation compounds of hydrotalcite-like anionic clays with anti-inflammatory agents, II: Uptake of diclofenac for a controlled release formulation, AAPS PharmSciTech., 3(3):E26 (2002).
Aoshima et al., Glycerin fatty acids esters as a new lubricant of tablets, Int. J. Pharm., 293:25-34 (2005).
Autissier et al., Relative in vitro efficacy of the phosphate binders lanthanum carbonate and sevelamer hydrochloride, J. Pharm. Sci., 96(10):2816-27 (2007).
Badawy et al., Effect of drug substance particle size on the characteristics of granulation manufactured in a high-shear mixer, AAPS PharmSciTech., 1(4):E33 (2000).
Badreddine et al.,Ion exchange of different phosphate ions into the zinc-aluminium-chloride layered double hydroxide, Materials Lett., 38(6): 391-5 (1999).
Barriga et al., Hydrotalcites as sorbent for 2,4,6-trinitrophenol: influence of the layer composition and interlayer anion, J. Mater. Chem., 12:1027-34 (2002).
Bolhuis et al., Interaction of tablet disintegrants and magnesium strearate during mixing I: effect on tablet disintegration, J. Pharm. Sci., 70(12):1328-30 (1981).
Bolognini et al., Mg/Al mixed oxides prepared by coprecipitation and sol-gel routes: a comparison of their physico-chemical features and performances in m-cresol methylation, Microporous and Mesoporous Materials, 66:77-89 (2003).
Bothwell, Overview and mechanisms of iron regulation, Nutrition Rev., 53:237-45 (Sep. 1995).
Brouwers et al., Biopharmaceutical tests on antacids: in vitro and in vivo studies, Drugs Under Experiment. Clin. Res., 5:55-61 (1997).
Brouwers et al., De invioed van de toedieningsvorm op de weringsduur en op het pH-Bereik bij antacida: een in-vitro en in-vivo studie,Pharmaceutisch Weekblad, 111:1244-8 (1976) (abstract only).
Brouwers, Liquid Antacids, Pharmaceutisch Weekblad, 110:337-51 (1975) (abstract only).
Budavari et al. (eds.), The Merck Index, pp. 277, 331, and 917, Merck & Co. (1996).
Carlino, Chemistry between the sheets, Chemistry in Britain, pp. 59-62 (Sep. 1997).
Chatelet et al., Competition between monovalent and divalent anions for calcined and uncalcined hydrotalcite: anion exchange and adsorption sites, Colloids and Surfaces A: Physiochemical and Engineering Aspects, 111:167-75 (1996).
Chitrakar et al., Adsorption of phosphate from seawater on calcined MgMn-layered double hydroxides, J. Colloid Interface Sci., 290(1): 45-51 (2005).
Cook, Adaptation in iron metabolism, Am. J. Clin. Nutr., 51(2):301-8 (1990).
Das et al., Adsorption of phosphate by layered double hydroxides in aqueous solutions, Appl. Clay Sci., 32(3-4:252-60 (2006).
de Roy et al., Antionic Clays: Trends in Pillaring Chemistry, chapter 7, pp. 108-169 IN: Synthesis of Microporous Mateirals (1992).
de Roy et al., Layered double hydroxides: synthesis and post-synthesis modification, Chapter I, pp. 33-34 IN: Rives (ed.), Layered Double Hydroxides: Present and Future, Nova Science Publishers, Inc. (2001), pp. 1-37.
de Roy et al., Surface Text and Electron Microscopy Studies, pp. 243-244 IN: Rives (ed.), Layered Double Hydroxides: Present and Future, Nova Science Publishers, Inc. (2001).
del Arco et al., Effect of the Mg:Al ratio on borate (or silicate)/nitrate exchange in hydrotalcite, J. Solid State Chem., 151(2):272-80 (2000).
del Arco et al., Surface and textural properties of hydrotalcite-like materials and their decomposition products, IN: Rouquerol et al. (eds.), Characterization of Porous Solids III, Studies in Surface Science and Catalysis, vol. 87, pp. 507-515 (1994).
Drueke, Lanthanum carbonate as a first-line phosphate binder: the "cons", Semin. Dial., 20(4):329-32 (2007).
Emmett, A comparison of clinically useful phosphorus binders for patients with chronic kidney failure, Kidney Int.,66:S25-S32 (2004).
Erickson et al., A study of structural memory effects in synthetic hydrotalcites using environmental SEM, Materials Lett., 59:226-9 (2005).
Evans et al., "Structural Aspects of Layered Double Hydroxides" pp. 1-12, IN: Duan et al. (eds.), Layered Double Hydroxides, vol. 119, Springer (2006).
Ferreira et al., Thermal decomposition and structural reconstruction effect on Mg Fe based hydrocalcite compounds, J. Solid State Chem., 177:3058-69 (2004).
Frost et al., Thermal decomposition of synthetic hydrotalcites reevesite and pyroaurite, J. Therm. Analysis Calorimetry, 76:217-25 (2004).
Grant et al. (eds.), Grant & Hackh's Chemical Dictionary, 5th edition, McGraw Hill, pp. 571 (1987).
Guillot et al., The use of magnesium-containing phosphate binders in patients with end-stage renal disease on maintenance hemodialysis, Nephron., 30(2): (1982), pp. 114-117.

(56) References Cited

OTHER PUBLICATIONS

Hansen et al., Formation of synthetic analogues of double metal-hydroxy carbonate minerals under controlled pH conditions: I. The synthesis of pyroaurite and reevesite, Clay Minerals, 25:161-79 (1990).
Hansen et al., Synthesis and characterization of pyroaurite, Appl. Clay Sci., 10(1-2):5-19 (1995).
Hansen et al., The use of glycerol intercalates in the exchange of $CO_3^{2-}$ with $SO_4^{2-}$, $NO^{3-}$ or $C_L$- in pyroaurite-type compounds, Clay Minerals, 26:311-27 (1991).
Hashi et al., Preparation and properties of pyroaurite-like hydroxy minerals, Clays and Clay Minerals, 31(2):152-4 (1983).
Hibino et al., Calcination and rehydration behavior of Mg—Fe—CO3 hydrotalcite-like compounds, J. Materials Sci. Lett., 19(16):1403-5 (2000).
International Specialty Products, Pharmaceuticals Solid Dosage Forms (2004), pp. 1-13.
Iranloye et al., Effects of compression force, particle size and lubricants on dissolution rate, J. Pharm. Sci., 67(4):535-9 (1978).
Ishimura et al., "Hyper- and Hypophosphataemia" pp. 149-158, IN: Morii et al. (eds.), Calcium in Internal Medicine, Springer (2002).
Kaplan et al., A preference study: calcium acetate tablets versus gelcaps in hemodialysis patients, Nephrol. Nurs. J., 29(4):363-5 (2002).
Kokot et al., A rotating disk study on the rates of hydrotalcite dissolution at 25° C., Pharmazie, 48 (H4):287-9 (1993).
Konorev et al., Selection of the optimal antacid drug in clinical practice, Consilium Medicum, vol. 5, issue 10 (2003), pp. 1-10.
Kostura et al., Rehydration of calcined Mg—Al hydrotalcite in acidified chloride-containing aqueous solution, Collect. Czech. Chem. Commun., 72:1284-94 (2007).
Kovanda et al., Thermal behavior of Ni—Mn layered double hydroxide and characterization of formed oxides, Solid State Sci., 5:1019-26 (2003).
Labajos et al., New layered double hydroxides with hydrotalcite structure containing Ni(II) and V(III), J. Materials Chem., 9:1033-9 (1999).
Larsson et al., Estimation of the bioavailability of iron and phosphorous in cereals using a dynamic in vitro gastrointestinal model, J. Sci. Food Agric., 74:99-106 (1997).
Lazaridis et al., Flotation of metal loaded clay anion exchangers, Part II: the case of arsenates, Chemosphere, 47:319-24 (2002).
Lazaridis et al., Flotation of metal loaded clay anion exchangers, Part II: the case of chromates, Chemosphere, 42:373-8 (2001).
Lazaridis, Sorption removal of anions and cations in single batch systems by uncalcined and calcined Mg—Al—CO3 hydrotalcite, Water Air Soil Pollution, 146:127-39 (2003).
Leinonen et al., Physical and lubrication properties of magnesium stearate, J. Pharm. Sci., 81(12):1194-8 (1992).
Li et al., Enteric-coated layered double hydroxides as a controlled release drug delivery system, Int. J. Pharm., 287(1-2):89-95 (2004).
Li et al., Stoichiometric Synthesis of Pure $MFe_2O_4$ (M=Mg, Co, and Ni) Spinel Ferrites from Tailored Layered Double Hydroxide (Hydrotalcite-Like) Precursors, Chem. Mater., 16(8):1597-602 (2004).
Linares et al., The influence of hydrotalcite and cancrinite type zeolite in acidic aspirin solutions, Microporous and Mesoporous Materials, 74:105-10 (2004).
Marchi et al., Impregnation-induced memory effect of thermally activated layered double hydroxide, Appl. Clay Sci., 13:35-48 (1998).
McCance et al., Absorption and excretion of iron, The Lancet, pp. 680-684 (Sep. 18, 1937).
McIntyre et al., Iron-magnesium hydroxycarbonate (Alpharen): a novel non calcium containing phosphate binder for the treatment of hyperphosphataemia in chronic haemodialysis patients, Nephrol. Dial. Transplant., 22 (suppl 6): vi171, FP452 Poster Session Abstract (Jun. 22, 2007).
Meng et al., Preparation and thermal decomposition of magnesium/iron (III) layered double hydroxide intercalated by hexacyanoferrate (III) ions, J. Mater. Sci., 39:4655-7 (2004).

Meng et al., Preparation of magnetic material containing MgFe2O4 spinel ferrite from a Mg—Fe(III) layered double hydroxide intercalated by hexacyanoferrate(III) ions, Mater.Chem. Phys., 86:1-4 (2004).
Miyata et al., Physiochemical properties of synthetic hydrotalcites in relation to composition, Clays and Clay Minerals, 28(1):50-6 (1980).
Murthy et al., Effect of shear mixing on in vitro drug release of capsule formulations containing lubricants, J. Pharm. Sci., 66(9):1215-9 (1977).
Naylor et al., Use of gastrointestinal model and gastroplus for the prediction of in vivo performance, Industrial Pharmacy, 12:9-12 (2006).
Newman et al., Comparative study of some layered hydroxide salts containing exchangable interlayer anions, J. Solid State Chem., 148:26-40 (1999).
O'Donovan et al., Substitution of aluminium salts by magnesium salts in control of dialysis hyperphosphataemia, The Lancet, pp. 880-881 (Apr. 19, 1986).
Oe et al., Long-term use of magnesium hydroxide as a phosphate binder in patients on hemodialysis, Clin. Nephrol., 28(4):180-5 (1987).
Ookubo et al., Hydrotalcites as potential adsorbents of intestinal phosphate, J. Pharm. Sci., 81 (11):1139-40 (1992).
Ookubo et al., Preparation and phosphate ion-exchange properties of a hydrotalcite-like compound, Langmuir, 9(5):1418-22 (1993).
Pesic et al., Thermal characteristics of a synthetic hydrotalcite like material, J. Mater. Chem., 2(10): (1992), pp. 1069-1073.
Powell et al., The chemistry between aluminum in the gastrointestinal lumen and its uptake and absorption, Proc. Nutrition Soc., 52:241-53 (1993).
Rajamathi et al., Reversable thermal behaviour of the layered double hydroxide of Mg with Al: mechanistic studies, J. Mater. Chem., 10:2754-7 (2000).
Raki et al., Preparation, Characterization, and Moessbauer Spectroscopy of Organic Anion Intercalated Pyroaurite-like Layered Double Hydroxides, Chem. Mater., 7(1):221-4 (1995).
Remuzzi et al., Hematologic consequences of renal failure, The Kidney, vol. II, 5th ed. pp. 2079-2102 (1996).
Rives, Study of Layered Double Hydroxides by Thermal Methods, chapter 4, pp. 116-133 IN: Rives (ed.), Layered Double Hydroxides: Present and Future, Nova Science Pub Inc. (2001).
Robolot et al., Effect of lubricant level and applied copressional pressure on surface friction of tablets, J. Pharm. Sci., 74(6):697-9 (1985).
Rodriguez-Benot et al., Mild hyperphosphatemia and mortality in hemodialysis patients, Am. J. Kidney Dis., 46(1):68-77 (2005).
Rubinstein et al., the effect of granule size on the in vitro and in vivo properties of bendrofluazide tables 5mg, Pharm. Acta Helv., 52 (1/2): XXX (1977).
Rudnic et al., Oral Solid Dosage Forms, chapter 45, pp. 858-890 IN: Gennaro (ed.), Remington: The Science and Practice of Pharmacy, 20th ed., Lippincott Williams & Wilkins (2000).
Sato et al., Adsorption of various anions by magnesium aluminum oxide Mg(0.7)Al(0.3)O(1.15), Ind. Eng. Chem. Prod. Res. Dev., 25:89-92 (1986).
Sato et al., Causticization of sodium carbonate with rock-salt-type magnesium aluminium oxide formed by the thermal decomposition of hydrotalcite-like layered double hydroxide, J. Chem. Tech. Biotechnol., 57:137-40 (1993).
Schwarz et al., Association of disorders in mineral metabolism with progression of chronic kidney disease, Clin. J. Am. Soc. Nephroi., 1:825-31 (2006).
Seida et al., Removal of phosphate by layered double hydroxides containing iron, Water Res., 36:1305-12 (2002).
Sheikh et al., Reducation of dietary phosphorus absorption by phosphorous binders: A theoretical, in vitro, and in vivo study, J. Clin. Invest., 83:66-73 (1989).
Shen et al., Preparation and characterization of Fe/MgO catalysts obtained from hydrotalcite-like compounds, Catalysis Today, 30(1-3):77-82 (1996).
Shin et al., Phosphorus removal by hydrotalcite-like compounds (HTLcs), Water Sci. Technol., 34(1-2):161-8 (1996).

(56) References Cited

OTHER PUBLICATIONS

Spengler et al., Cross-linked iron dextran is an efficient oral phosphate binder in the rat, Nephrol. Dial. Transplant., 11(5):808-12 (1996).
Stamatakis et al., Influence of pH on in vitro disintegration of phosphate binders, Am. J. Kidney Dis., 32(5):808-12 (1998).
Suren, Evaluation of lubricants in the development of tablet formulation, Dansk TIDSskr. Farm 45, pp. 331-338 (1971).
Tezuka et al, The Synthesis and Phosphate Adsorptive Properties of Mg(II)—Mn(III) Layered Double Hydroxides and Their Heat-Treated Materials, Bull Chem. Soc. Jpn. 2004, 77:2101-7 (2004).
The National Kidney Foundation Kidney Disease Quality Outcomes Initiative, Clinical Practice Guidelines for Bone Metabolism and Disease in Chronic Disease, Guide 5 pp. 1, pt. 5.5 (2003).
Tichit et al., Catalysis by hydrotalcites and related materials, Cattech, 7(6):206-17 (2003).
Titulaer et al., The formation of ice between hydrotalcite particles measured by thermoporometry, Clay Minerals, 31(2):263-77 (1996).
Trifiro et al, "Hydrotalcite-like Anionic Clays (Layered Double Hydroxides)", vol. 7, chapter 8, pp. 251-291, IN: Alberti et al. (eds.) Comprehensive Supramolecular Chemistry, Pergamon, Oxford (1996).
Ulibarri et al., Kinetics of the thermal dehydration of some layered hydroxycarbonates, Thermochimica Acta, 135:231-6 (1998).
USANA Technical Bulletin, Tablet Excipients, Jun. 1999.
Van Der Voet et al., Intestinal absorption of aluminium from antacids: a comparison between hydrotalcite and algeldrate, Clin. Tech., 24(6):545-3 (1986).
Vatier et al., Antacid activity of calcium carbonate and hydrotalcite tablets, Arzneim-Forsch/Drug Res., 44(4):514-8 (1994).
Vitkova et al., The use of some hydrophobic substances in tablet technology, Milan Chilabala, Acta Pharamceutica Hungaria, 68:336-44 (1998).
Zhang et al., Phosphorous anion exchange characteristic of a pyroaurite-like compound, Inorg. Mater., 4:132-8 (1997).
Zhang et al., Synthesis of Mg/Fe pyroaurite-like compounds and their anion-exchange characteristics, Inorg. Mater., 2(259):480-5 (1995).
Zhang et al., Synthesis and characterization of a novel nanoscale magnetic solid base catalyst involving a layered double hydroxide supported on a ferrite core, J. Solid State Chem., 177:772-80 (2004).
Zhao et al., Preparation of layered double-hydroxide nanomaterials with a uniform crystalite size using a new method involving separate nucleation and aging steps, Chem. Mater., 14(10):4286-91 (2002).
Zhu et al., Adsorption of phosphate by hydrotalcite and its calcined product, Acta Mineralogica Sinica, 25(1):27-32 (2005).
de Roy et al., Layered double hydroxides: synthesis and postsynthesis modification, Chapter I, pp. 33-34 IN: Rives (ed.), Layered Double Hydroxides: Present and Future, Nova Science Publishers, Inc. (2001).
He et al., Preparation of layered double hydroxides, Struct. Bond., 119:89-119 (2006).
Llewellyn et al., The binding of bile acids by hydrocalcite and other antacid preparations, Pharmaceutica Acta Helvetiae, 52(1/2):1-5 (1977).
Logham-Adham, Safety of new phosphate binders for chronic renal failure, Drug Safety, 26(15):1093-1115 (2003).
Merck Index, p. 969, entries 5694-5707 (1996).

Reichle, Synthesis of anionic clay minerals (mixed metal hydroxides, hydrotalcite), Solid State Ionics, 22(1):135-41 (1986).
Sigma-Aldrich product information for Iron(III) nitrate nonanhydrate, retrieved from the Internet: <http:www.sigmaaldrich.com> on Jun. 11, 2012 (one page).
Cargill et al., Chemical reactivity of aluminium-based pharmaceutical compounds used as phosphate-binders, J. Pharm. Pharmacol., 41:11-16 (1989).
Lin, Mei-Shu; Sun, Pin; Yu, Hsiu-Ying. School of Pharmacy, College of Medicine, National Taiwan University, Taipei, Taiwan. Evaluation of buffering capacity and acid neutralizing-pH time profile of antacids. Journal of the Formosan Medical Association (1998), 97(10), 704-710.
Adams et al., Formulation of a sterile surgical lubricant, J. Pharm. Pharmacol., 24 Suppl:178P (1972).
Brauner, Das atomgewicht des lanthans, Zeitschrift fur Anorganische Chemie, 33(1):317-21 (1902).
Dewberry et al., "Lanthanum carbonate: A novel non-calcium containing phosphate binder", *J Am Soc Nephrol*, 8:A2610 (1997).
Entry for "obtainable", Collins English Dictionary, retrieved from the Internet at <http://www.collinsdictionary.com> on May 15, 2013.
European Search Report for European application No. EP 06013811, dated Jun. 27, 2007.
Fernandez et al., The effect of iron on the crystalline phases formed upon thermal decomposition of Mg—Al—Fe hydrotalcites, RCS Publishing: Journal of Materials Chemistry, 8(11):2507-14 (1998).
Forano, Environmental remediationinvolving layered double hydroxides, pp. 426-458, vol. 1, Elsevier Interface Science and Technology (2004).
Goh et al., Application of layered double hydroxides for removal of oxyanions: a review, Water Res., 42:1343-68 (2008).
Hansen et al., Reduction of nitrate to ammonium by sulphate green rust: activation energy and reaction mechanism, Clay Minerals, 33:87-101 (1998).
He et al., Hydrothermal Methods, p. 108 IN: Duan et al. (eds.), Layered Double Hydroxides, Springer-Verlag Berlin Heidelberg (2006).
Merriam-Webster's Collegiate Dictionary—11th edition, entry for "prophylaxis" on p. 996 (2004).
Mesh to Micron Conversion chart, retrieved from the Internet at <http://www.shomegold.org/news/Mesh.html>, accessed Sep. 27, 2012.
Rankin et al., The development and in-vitro evaluation of novel mixed metal hydroxy-carbonate compounds as phosphate binders, J. Pharm. Pharmacol., 53:361-9 (2001).
Remuzzi et al., Hematologic consequences of renal failure, Chapter 50, pp. 2079-2102 IN: Rose, Pathophysiology of Renal Disease, McGraw-Hill (1987).
Toth et al., Nano-scaled inorganic/biopolymer composites: molecular modeling vistas (2005).
Toth et al., Structure and energetics of biocompatible polymer nanocomposite systems: a molecular dynamics study, Biomacromolecules, 7:1714-9 (2006).
Tsuji et al., Hydrotalcites with an extended $Al^{3+}$-substitution: synthesis, simultaneous TG-DTA-MS study, and their $CO_2$ adsorption behaviors, J. Mater. Res., 8(5):1137-42 (1993).
Toth et al., Nano-scaled inorganic/biopolymer composites: molecular modeling vistas, AIChE Annual Meeting (2005).

* cited by examiner

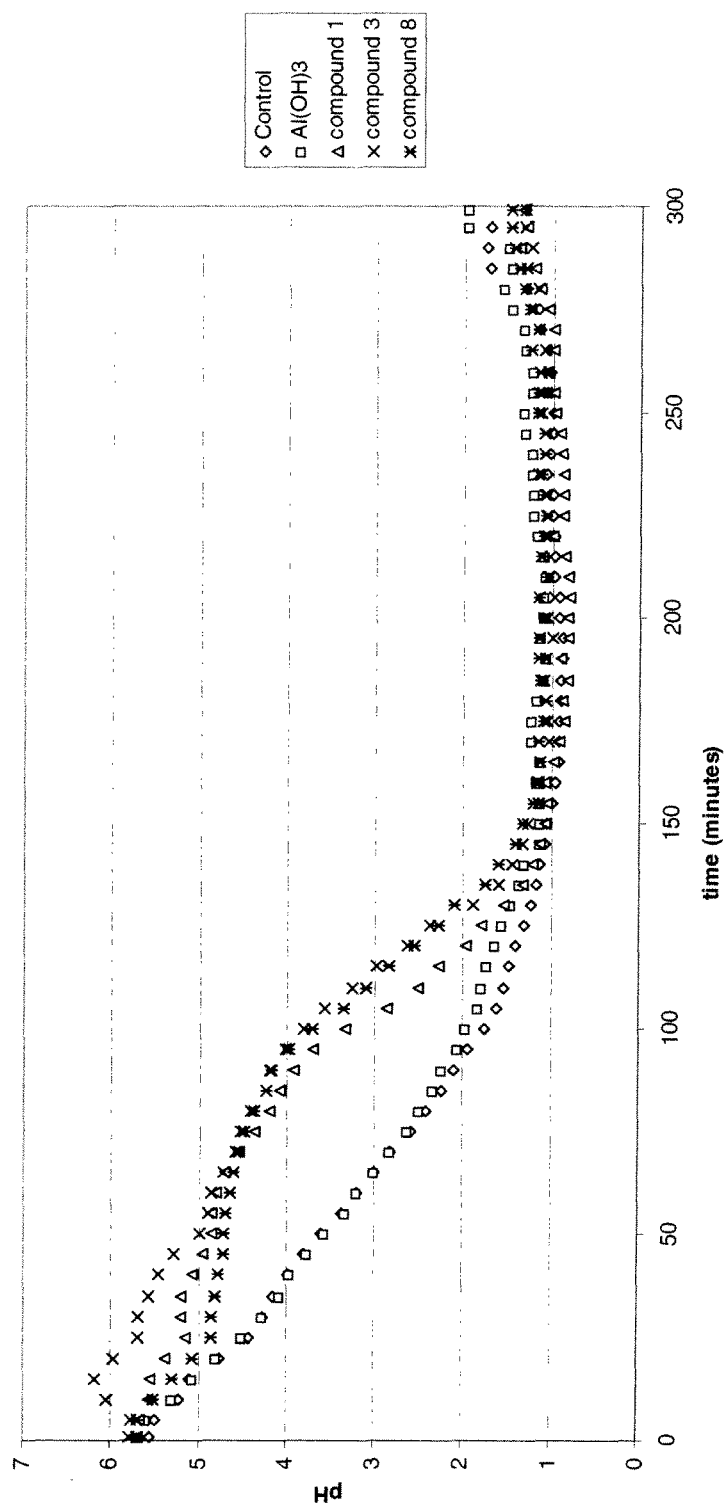

MIXED METAL COMPOUNDS USED AS ANTACIDS

FIELD

The present invention relates to the use of a compounds as an antacid. It further extends to the use of such compounds for the treatment of conditions or diseases associated with adverse stomach acid levels, such as peptic ulcers, dyspepsia, heartburn, acid indigestion or acid reflux.

BACKGROUND

The two major products secreted by the stomach, hydrochloric acid and pepsin (a protease), both participate in protein digestion. Hydrochloric acid helps dissolve the particulate matter in food and provides an optimal pH for the activity of pepsin. Frequent occurrence of elevated levels of gastric acid and pepsin can lead to aggravation of the lining of the stomach resulting in digestion of the mucosal cells and leading to peptic ulcers Peptic ulcers are perforations in the mucous membrane where the lining of the stomach (gastric ulcers) or duodenum (duodenal ulcers) is exposed to the acidic contents of the stomach. When gastric hydrochloric acid reaches the exposed nerve in the ulcers they signal pain to the central nervous system. The gastric acid may also cause ulcers in the oesophagus.

Antacids relieve the symptoms of peptic ulcers by performing a neutralization reaction, i.e. they buffer gastric acid, raising the pH to reduce acidity in the stomach. Antacids also relieve heartburn (hydrochloric acid from the stomach entering into the oesophagus). Hydrotalcite (MgAl) antacids have also been reported by Playle et al to relieve symptoms by inhibiting pepsin activity and are also believed to provide mucosal protection by its ability to mimic the properties of the gastric mucus gel.

Examples of antacids are $Al(OH)_3$, $Mg(OH)_2$, Ca Carbonate, and MgAl hydrotalcite. Although effective, antacids may give rise to new problems.

Some antacids are known to stop digestion of protein in the stomach by raising the pH to above 7, which may irreversibly inactivate pepsin. Undigested protein in the GI tract can then cause a multitude of problems including gas, bloating and constipation. The presence of food may also increase the gastric pH and levels of gastrin, consequently the combination of food and certain types of antacid may lead to a sudden increase in the gastric pH above 7 before the stomach empties and the pH decreases again. It is desirable that a compound used in the treatment of gastric ulcer should not only be an effective acid buffering agent, but should also avoid sudden changes in gastric pH. Furthermore, an antacid should inhibit pepsin but not too much so that pepsin may be irreversibly inactivated.

A further problem of antacids is that they may cause an 'acid rebound effect' because a 'biological switch' or feedback mechanism exists in the stomach. For example, if the gastric pH is at a high pH value then the hormone gastrin is stimulated which in turn stimulates further acid secretion in which the gastric acid returns in greater concentration. Consequently, this may lead a positive feed-back loop and thus requiring further use of antacids. This is associated with antacids with the most rapid onset of action whereby the pH is suddenly increased to a higher pH value (typically above pH 5).

It is also known that excess acid (typically below pH 3) can aggravate ulcers; pain can occur when the acid irritates the exposed nerves in the ulcers. Consequently, the optimum range to which antacids should buffer gastric pH is between pH 3-4.5 when taken without food and should not exceed pH 7 in the presence of food.

Particular antacids are also known to cause problems

Magnesium hydroxides has laxative properties, may release significant amounts of magnesium and can lead to sudden changes to higher gastric pH values (ie above pH 7).

Regular doses of high levels of carbonates (typically generated by some carbonate-based antacids such as Ca carbonate) may cause alkalosis.

MgFe or MgAl hydrotalcites may contain carbonate but typically at lower level (<100 g $CO_3$/kg) than contained in $CaCO_3$ (600 g $CO_3$/kg) or $MgCO_3$ (710 g $CO_3$/kg)

MgAl hydrotalcites are believed to avoid the acid rebound effect and have been reported to provide mucosal protection. However, the absorption of $Al^{3+}$ from antacids based on aluminium is a concern. This may result in Al accumulation in the body to toxic levels.

Some antacids have high sodium content and should be avoided by those on a low sodium diet.

Hydrotalcite-type materials may be preferred as they have a dual action. It is hypothesised that stomach acid reacts rapidly with hydrotalcite via anion exchange neutralisation to yield the chloride form of the compound. The mineral then further reacts with physiological fluid to slowly disintegrate the mineral skeleton thereby providing long term buffering. This dual action results in a compound providing rapid relief from acute indigestion, and the prolonged action required for recurring dyspepsia.

An increase in surface area of either the hydrotalcite-crystallites or -particles would be expected to cause an increase in rate of reaction. The larger the crystallites, and the larger the particle size, the longer the time before dissolution of the hydrotalcite by attack of acid at the site of the hydroxide ions. Furthermore, it is believed that small particles are more readily dispersed through the meal. The buffering ability depends therefore both on the crystallite size and the particle size.

Tablet disintegration is another important factor for tablets containing antacids. Antacids are not intended to be absorbed into blood but rather act locally within the gastro-intestinal tract and are dosed as an inorganic solid dose form. In these instances, tablet disintegration needs to provide the antacid particles with an increased surface area. The increased surface area is typically obtained by chewing the tablet.

Tabletting MgAl hydrotalcites significantly reduces their acid neutralization capacity and speed by the reduction in availability of particle surface area resulting from the tablet compression.

Consequently, hydrotalcites have been made commercially available only as chewable tablets or as liquid suspensions up to now. MgAl Hydrotalcites that are commercially available include Talcid Plus-tablets or -liquids, Ultacit, Talidat and Altacit Plus liquid.

Chewable tablets and liquid suspensions tend to have shorter residence times in the stomach than other dose forms such as non-chewable tablets. The duration of the antacid effect is very strongly dependent on the emptying rate of the stomach. Taken on an empty stomach, antacids tend to only neutralize acid for 30 to 60 minutes because the antacid quickly leaves the stomach whereas if taken with food, the protective effect may last as long as 2 or 3 hours. However, some antacids may not work in the presence of food because of drug-food interactions competing with its antacid functionality.

Hydrotalcite powders typically display poor flowability characteristics especially when in fine powder form; however, more coarse material results in inhibition of antacid performance (see Table 1). Powders of poor flowability are typically characterised as being cohesive, having a high Hausner ratio, moderate to high wall friction angles and a tendency to develop significant shear strength under compaction. Poor flowability properties result in difficulties in filling capsules or manufacturing tablets on an industrial scale especially when a high content of the hydrotalcite material is required in the dose-unit.

Chewable tablets of antacids may result in an unpleasant taste due to chalkiness, bitter or metallic taste, grittiness, dryness and astringent properties of these materials. Chewable tablets could result in dental problems and it is more difficult to taste-mask the active ingredient. Furthermore, patients do not chew tablets uniformly which could result in variation of the effectiveness of the antacid. Liquid suspensions have the disadvantage of storage and convenience and are less portable. In addition, these dose forms deliver the active ingredient more rapidly which in turn could increase the likelihood of the acid-rebound effect occurring.

It has been suggested to coat antacid tablets with a coating material which will not dissolve in the mouth but will dissolve in the stomach. However, many coatings dissolve in the intestine and not the stomach and thus deliver the antacid at the wrong site. Moreover, although a coating may be used which dissolves in the stomach, the rate of dissolution may not be fast enough to allow for sufficient neutralizing gastric acid time before the antacid is removed from the stomach by gastric emptying. However, if the dissolution is too fast then the initial gastric acid fluid pH may rise too rapidly thereby causing the so-called acid-rebound effect.

$H_2$ receptor antagonists or proton pump inhibitors are capable of blocking the acid production of the stomach over a period of several hours. However, the risk of side-effects can be more severe as these drugs are distributed throughout the entire body via the blood. $H_2$ receptor or proton pump inhibitors antagonist are therefore not generally able to replace the antacids which have a lower risk of side-effects.

SUMMARY OF INVENTION

Thus, a first aspect of the present invention provides use of a mixed metal compound in the manufacture of medicament for neutralising or buffering stomach acid, wherein the mixed metal compound contains
at least one trivalent metal selected from iron (III) and aluminium and
at least one divalent metal selected from of magnesium, iron, zinc, calcium, lanthanum and cerium,
wherein
(A) the mixed metal compound is of formula (I):

$$M^{II}_{1-a}M^{III}_{a}O_{b}A^{n-}_{c}\cdot zH_2O \qquad (I)$$

where $M^{II}$ is the at least one bivalent metal;
$M^{III}$ is the at least one trivalent metal;
$A^{n-}$ is at least one n-valent anion;

$$2+a=2b+\Sigma cn,$$

$\Sigma cn<0.9a$, and
z is 2 or less,
and/or
(B) the mixed metal compound is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient.

A second aspect of the invention provides use of a mixed metal compound in the manufacture of medicament for use in the therapy of a condition or disease associated with adverse stomach acid levels, wherein the mixed metal compound contains at least one trivalent metal selected from iron (III) and aluminium and at least one divalent metal selected from of magnesium, iron, zinc, calcium, lanthanum and cerium,
wherein
(A) the mixed metal compound is of formula (I):

$$M^{II}_{1-a}M^{III}_{a}O_{b}A^{n-}_{c}\cdot zH_2O \qquad (I)$$

where $M^{II}$ is the at least one bivalent metal;
$M^{III}$ is the at least one trivalent metal;
$A^{n-}$ is at least one n-valent anion;

$$2+a=2b+\Sigma cn,$$

$\Sigma cn<0.9a$, and
z is 2 or less,
and/or
(B) the mixed metal compound is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient.

A third aspect of the invention provides a mixed metal compound for use for neutralising or buffering stomach acid, wherein the mixed metal compound contains
at least one trivalent metal selected from iron (III) and aluminium and
at least one divalent metal selected from of magnesium, iron, zinc, calcium, lanthanum and cerium,
wherein
(A) the mixed metal compound is of formula (I):

$$M^{II}_{1-a}M^{III}_{a}O_{b}A^{n-}_{c}\cdot zH_2O \qquad (I)$$

where $M^{II}$ is the at least one bivalent metal;
$M^{III}$ is the at least one trivalent metal;
$A^{n-}$ is at least one n-valent anion;

$$2+a=2b+\Sigma cn,$$

$\Sigma cn<0.9a$, and
z is 2 or less,
and/or
(B) the mixed metal compound is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient.

A fourth aspect of the invention provides a mixed metal compound for use in the therapy of a condition or disease associated with adverse stomach acid levels, wherein the mixed metal compound contains at least one trivalent metal selected from iron (III) and aluminium and at least one divalent metal selected from of magnesium, iron, zinc, calcium, lanthanum and cerium, wherein
(A) the mixed metal compound is of formula (I):

$$M^{II}_{1-a}M^{III}_{a}O_{b}A^{n-}_{c}\cdot zH_2O \qquad (I)$$

where $M^{II}$ is the at least one bivalent metal;
$M^{III}$ is the at least one trivalent metal;
$A^{n-}$ is at least one n-valent anion;

$$2+a=2b+\Sigma cn,$$

$\Sigma cn<0.9a$, and
z is 2 or less,
and/or
(B) the mixed metal compound is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient.

References herein to "granules" equally apply to the "granular material" of the present invention.

It has been found that surprisingly, mixed metal compounds used in accordance with the present invention provide antacids with one or more of the following properties:
  non-chewable form
  high active ingredient content
  does not release or reduces release of aluminium
  reduces release of magnesium, calcium, iron, zinc, or carbonate ions
  maintains a stomach pH that is neither too acidic or alkaline (buffers to the optimum pH range of between pH 3-4.5).
  does not cause or reduces acid rebound effect
  can be taken with or without food
  does not stop digestion of food
  provide mucosal protection
  low sodium content (ie containing less than 1 mmol sodium per tablet or 10 ml dose)
  is not rapidly emptied from the stomach
  rapid onset of action, a high buffering capacity and a long duration of action
  provision of smaller tablet size The water content of the granules for use in the present invention is expressed in terms of the content of non-chemically bound water in the granules. This non-chemically bound water therefore excludes chemically bound water. Chemically bound water may also be referred to as structural water.

The amount of non-chemically bound water is determined by infra-red balance. Moisture determination was carried out using a Satorius MA30 infra-red balance set at 75° C. with automatic endpoint determination. The Satorius settings have been shown to be equivalent to drying to constant weight at 105° C. in an oven. The weight equivalent of non-chemically bound water driven off can then be calculated as a weight percentage of the granules.

In one aspect, the granular material is provided in a unit dose for oral administration comprising a water-resistant capsule containing granular material described herein.

In one aspect, the granular material is provided in a unit dose for oral administration comprising a compacted tablet of granular material described herein. Preferably, the tablet is coated with a water-resistant coating.

Preferred methods of forming the granular material and further preferred aspects of the unit doses are described in WO2007088343.

The water-resistant capsule for use in of the invention is suitably a hard gelatine capsule. For the water-resistant capsule, by water-resistant it is meant that on storage for 4 weeks at 40° C. and 75% relative humidity, the water uptake of the unit dose, (i.e. the capsule containing the granules of the first aspect of the invention), due to moisture content change is preferably less than 10% more preferably less than 5% by weight of the unit dose. Such capsules have the advantage of helping stabilise the moisture content of the granules on storage The tablets for use in the invention preferably have a water-resistant coating in order to inhibit moisture ingress into the tablet or moisture loss from the tablet on storage. However, the water resistant coating must allow break-up of the tablet after a suitable time following ingestion such that the mixed metal compound can be effective in the gut of the patient. By water-resistant it is meant that on storage for 4 weeks at 40° C. and 75 relative humidity, the water uptake of the coated tablet due to moisture content change is preferably less than 10% more preferably less than 5% by weight of the coated tablet. In a preferred aspect by water-resistant it is meant that on storage for 12 months at 25° C. and 65% relative humidity, the water uptake of the coated tablet due to moisture content change is preferably less than 10% more preferably less than 5% by weight of the coated tablet. In a further preferred aspect by water-resistant it is meant that on storage for 12 months at 30° C. and 65% relative humidity, the water uptake of the coated tablet due to moisture content change is preferably less than 10% more preferably less than 5% by weight of the coated tablet. In a preferred aspect by water-resistant it is meant that on storage for 6 months at 40° C. and 75% relative humidity, the water uptake of the coated tablet due to moisture content change is preferably less than 10% more preferably less than 5% by weight of the coated tablet.

DETAILED DESCRIPTION AND PREFERRED EMBODIMENTS

As discussed, the present invention provides use of a mixed metal compound in the manufacture of medicament for neutralising or buffering stomach acid, wherein the mixed metal compound contains
at least one trivalent metal selected from iron (III) and aluminium and
at least one divalent metal selected from of magnesium, iron, zinc, calcium, lanthanum and cerium,
wherein
(A) the mixed metal compound is of formula (I):

$$M^{II}_{1-a}M^{III}_{a}O_{b}A^{n-}_{c}\cdot zH_2O \qquad (I)$$

where $M^{II}$ is the at least one bivalent metal;
$M^{III}$ is the at least one trivalent metal;
$A^{n-}$ is at least one n-valent anion;

$$2+a=2b+\Sigma cn,$$

$\Sigma cn<0.9a$, and
z is 2 or less,
and/or
(B) the mixed metal compound is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient.

The value of c for each anion is determined by the need for charge neutrality as expressed by the formula $2+a=2b+\Sigma cn$.

It will be appreciated that in one preferred aspect, the mixed metal compound is of formula (I):

$$M^{II}_{1-a}M^{III}_{a}O_{b}A^{n-}_{c}\cdot zH_2O \qquad (I)$$

where $M^{II}$ is the at least one bivalent metal;
$M^{III}$ is the at least one trivalent metal;
$A^{n-}$ is at least one n-valent anion;

$2+a=2b+\Sigma cn,$ $\Sigma cn<0.9a$, and
z is 2 or less,

The compound of formula (I) is typically obtainable or is obtained by heating a starting material comprising a layered double hydroxides, hydrotalcite or pyroraurite structure at a temperature of from 200° C. to 600° C., preferably the heating may be performed at a temperature of from 250° C. to 500° C.

The compound of formula (I) is typically obtainable or is obtained by heating a starting material comprising a layered double hydroxide structure at a temperature of from 200° C. to 600° C., preferably the heating may be performed at a temperature of from 250° C. to 500° C.

The starting material preferably comprises a compound of formula (II):

$$M^{II}_{1-x}M^{III}_{x}(OH)_2 A^{n-}_{y}\cdot mH_2O \qquad (II)$$

wherein $M^{II}$ is the at least one bivalent metal;
$M^{III}$ is the at least one trivalent metal;
$A^{n-}$ is at least one n-valent anion;

$x=\Sigma yn$ $0<x\leq0.4$,
$0<y\leq1$ and
$0<m\leq10$.

In formula (I) the value of z is suitably 2 or less, more preferably 1.8 or less, even more preferably 1.5 or less. The value of z may be 1 or less In formula (I) the value of a may be from 0.2 to 0.4. In formula (I) a may be <0.3. The value of a may be 0.1 to 0.4, preferably 0.2 to 0.45. Preferably the value of a is from 0.1 to 0.34, preferably 0.2 to 0.34.

In formula (I) the value of b is suitably 1.5 or less, preferably 1.2 or less. The value of b is preferably greater than 0.2, more preferably greater than 0.4, even more preferably greater than 0.6, most preferably greater than 0.9.

When a is ≤0.3 it is preferred that $\Sigma cn<0.7a$. Thus in formula (I) in one aspect $0.03a<\Sigma cn<0.7a$. In a further aspect in formula (I) $0.03a<\Sigma cn<0.5a$.

The value of c for each anion is determined by the need for charge neutrality as expressed by the formula $2+a=2b+\Sigma cn$.

It will be appreciated that in one preferred aspect, the mixed metal compound is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient. The value of c for each anion is determined by the need for charge neutrality as expressed by the formula $2+a=2b+\Sigma cn$.

The mixed metal compound provided in the form of a granular material is preferably of formula (III):

$$M^{II}_{1-x}M^{III}_{x}(OH)_2 A^{n-}_{y}\cdot mH_2O \qquad (III)$$

where $M^{II}$ is the at least one bivalent metal;
$M^{III}$ is the at least one trivalent metal;
$A^{n-}$ is at least one n-valent anion;

$x=\Sigma ny;$ $0<x\leq0.4$,
$0<y\leq1$, and
$0\leq m\leq 10$.

In one preferred aspect $0<x\leq 0.4$. In one preferred aspect $0.1<x\leq 0.4$, such as $0.2<x\leq 0.4$, or $0.3<x\leq 0.4$, 0.4. It will be understood that $x=[M^{III}]/([M^{II}]+[M^{III}])$ where $[M^{II}]$ is the number of moles of $M^{II}$ per mole of compound of formula I and $[M^{III}]$ is the number of moles of $M^{III}$ per mole of compound of formula I.

In one preferred aspect $0<y\leq 1$. Preferably $0<y\leq 0.8$. Preferably $0<y\leq 0.6$. Preferably $0<y\leq 0.4$. Preferably $0.05<y\leq 0.3$. Preferably $0.05<y\leq 0.2$. Preferably $0.1<y\leq 0.2$. Preferably $0.15<y\leq 0.2$.

In one preferred aspect $0\leq m\leq 10$. Preferably $0\leq m\leq 8$. Preferably $0\leq m\leq 6$. Preferably $0\leq m\leq 4$. Preferably $0\leq m\leq 2$. Preferably $0.1\leq m\leq 2$. Preferably $0.5\leq m\leq 2$. Preferably $1\leq m\leq 2$. Preferably $1\leq m\leq 1.5$. Preferably $1\leq m\leq 1.4$. Preferably $1.2\leq m\leq 1.4$. Preferably m is approximately 1.4.

Preferably, $0<x\leq 0.4$, $0<y\leq 1$, and $0\leq m\leq 10$.

It will be appreciated that each of the preferred values of x, y and m may be combined. Thus any combination of each of the values listed in the table below are specifically disclosed herein and may be provided by the present invention.

| X | y | m |
|---|---|---|
| $0.1 < x \leq 0.4$ | $0 < y \leq 0.8$ | $0 \leq m \leq 10$ |
| $0.2 < x \leq 0.4$ | $0 < y \leq 0.6$ | $0 \leq m \leq 8$ |
| $0.3 < x \leq 0.4$ | $0 < y \leq 0.4$ | $0 \leq m \leq 6$ |
| $0.3 \leq x \leq 0.4$ | $0.05 < y \leq 0.3$ | $0 \leq m \leq 4$ |
| $0 < x \leq 0.4$ | $0.05 < y \leq 0.2$ | $0 \leq m \leq 2$ |
| | $0.1 < y \leq 0.2$ | $0.1 \leq m \leq 2$ |
| | $0.15 < y \leq 0.2$ | $0.5 \leq m \leq 2$ |
| | | $1 \leq m \leq 2$ |
| | | $1 \leq m \leq 1.5$ |
| | | $1 \leq m \leq 1.4$ |
| | | $1.1 \leq m \leq 1.4$ |

In the above formula (III), when A represents more than one anion, the valency (n) of each may vary. "$\Sigma ny$" means the sum of the number of moles of each anion multiplied by its respective valency.

Crystallite Size

Crystallite size of the powders of formula (II) or (III) was determined from powder x-ray diffractometry spectra (XRD) line broadening and calculated using the so-called Scherrer equation (instrumental broadening factors have not been taken into account). The line broadening is a function of the average size of the crystallites.

Suitably, the crystallite size of the compounds of formula (II) or (III) is preferably less than 200 Å, more preferably less than 175 Å, even more preferably less than 150 Å, most preferably less than 100 Å.

Typically, smaller crystallites are obtained by not growing the crystals further. This is typically achieved by avoiding a hydrothermal ageing process (i.e. one where the reaction slurry is either heated or left to stand for a prolonged time period)

Preferably compound of formula (I) was prepared from the unaged form of compound (II).

Granules

The granules for use in the present invention comprise at least 50%, preferably at least 60%, more preferably at least 70% most preferably at least 75%, by weight mixed metal compound.

The granules of the present invention comprise from 3 to 12% by weight of non-chemically bound water, preferably from 5 to 10% by weight.

The remainder of the granules may comprise a pharmaceutically acceptable carrier for the mixed metal compound, chiefly an excipient or blend of excipients, which provides the balance of the granules. Hence the granules may comprise no greater than 47% by weight of excipient. Preferably the granules comprise from 5 to 47% by weight of excipient, more preferably from 10 to 47% by weight of excipient, more preferably from 15 to 47% by weight of excipient.

The mixed metal compound provided in the form of a granular material ideally has less than 15% by weight crystallite water. Preferred amounts of crystallite water are less than 10% by weight. The mixed metal compound provided in the form of a granular material has less than 15% by weight crystallite-surface absorbed water, or less than 10% by weight crystallite-surface absorbed water, or less than 1% by weight crystallite-surface absorbed water.

Granule Size

Suitably, at least 90% by weight of the granules have a diameter less than 1180 micrometers as measured by sieving.

Preferably, at least 50% by weight of the granules have a diameter less than 710 micrometers as measured by sieving.

More preferably, at least 50% by weight of the granules have a diameter from 106 to 1180 micrometers, preferably from 106 to 500 micrometers.

Even more preferably, at least 70% by weight of the granules have a diameter from 106 to 1180 micrometers, preferably from 106 to 500 micrometers.

Preferably the weight median particle diameter of the granules is from 200 to 400 micrometers.

Larger granules can lead to slow pH buffering (Table 1). Too high a proportion of granules less than 106 micrometers in diameter can lead to the problem of poor flowability of the granules. Preferably, at least 50% by weight of the granules have a diameter greater than 106 micrometers as measured by sieving, more preferably at least 80% by weight.

Granule Ingredients

Suitable excipients which may be included in the granules include conventional solid diluents such as, for example, lactose, starch or talcum, as well as materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, lactose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

The term excipient herein also includes auxiliary components such as tablet structurants or adhesives, disintegrants or swelling agents.

Suitable structurants for tablets include acacia, alginic acid, carboxymethylcellulose, hydroxyethylcellulose, hydroxypropylcellulose, dextrin, ethylcellulose, gelatin, glucose, guar gum, hydroxypropylmethylcellulose, kaltodextrin, methylcellulose, polyethylene oxide, povidone, sodium alginate and hydrogenated vegetable oils.

Suitable disintegrants include cross-linked disintegrants. For example, suitable disintegrants include cross-linked sodium carboxymethylcellulose, cross-linked hydroxypropylcellulose, high molecular weight hydroxypropylcellulose, carboxymethylamide, potassium methacrylatedivinylbenzene copolymer, polymethylmethacrylate, cross-linked polyvinylpyrrolidone (PVP) and high molecular weight polyvinylalcohols.

Cross-linked polyvinylpyrrolidone (also known as crospovidone, for example available as Kollidon CL-M™ ex BASF) is an especially preferred excipient for use in the tablets of the invention. Suitably, the granules of the tablets of the invention comprise from 1 to 15% by weight of cross-linked polyvinylpyrrolidone, preferably from 1 to 10%, more preferably from 2 to 8%. Preferably, the cross-linked polyvinylpyrrolidone has a $d_{50}$ weight median particle size, prior to granulation of less than 50 micrometers (i.e. so-called B-type cross-linked PVP). Such material is also known as micronised crospovidone. It has been found that the cross-linked polyvinylpyrrolidone at these levels leads to good disintegration of the tablet but with less pH buffering as compared to some other excipients. The preferred sizes for the cross-linked polyvinylpyrrolidone give reduced grittiness and hardness of the particles formed as the tablets disintegrate.

Another preferred excipient for use in the granules of the tablets is pregelatinised starch (also known as pregelled starch). Preferably, the granules comprise from 5 to 20% by weight of pregelled starch, more preferably 10 to 20%, even more preferably from 12 to 18% by weight. The pregelatinised starch at these levels improves the durability and cohesion of the tablets without impeding the disintegration of the tablets in use. The pregelatinised starch is suitably fully pregelatinised, with a moisture content from 1 to 15% by weight and a weight median particle diameter from 100 to 250 micrometers. A suitable material is Lycotab™—a fully pregelatinised maize starch available from Roquette.

A combined excipient including both pregelatinised starch and crospovidone is particularly preferred, as this combination of excipients gives the ability to reliably form compacted tablets of various shapes, good granule homogeneity and good disintegration characteristics from the granules of the invention.

The granules may also comprise preservatives, wetting agents, antioxidants, surfactants, effervescent agents, colouring agents, flavouring agents, pH modifiers, sweeteners or taste-masking agents. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include sodium hydrogencarbonate (i.e. bicarbonate), citric acid, tartaric acid, hydrochloric acid and maleic acid. Suitable sweeteners include aspartame, acesulfame K and thaumatin. Suitable taste-masking agents include sodium hydrogencarbonate, ion-exchange resins, cyclodextrin inclusion compounds and adsorbates. Suitable wetting agents include sodium lauryl sulphate and sodium docusate. A suitable effervescent agent or gas producer is a mixture of sodium bicarbonate and citric acid.

Granulation

Granulation may be performed by a process comprising the steps of:
i) mixing the mixed metal compound with one or more excipients to produce a homogeneous mix,
ii) contacting a suitable liquid with the homogeneous mix and mixing in a granulator to form wet granules,
iii) optionally passing the wet granules though a screen to remove granules larger than the screen size,
iv) drying the wet granules to provide dry granules.
v) milling and/or sieving the dry granules.

Suitably the granulation is by wet granulation, comprising the steps of;
i) mixing the mixed metal compound with suitable excipients to produce a homogeneous mix,
ii) adding a suitable liquid to the homogeneous mix and mixing in a granulator to form granules,
iii) optionally passing the wet granules though a screen to remove granules larger than the screen size,
iv) drying the granules.
v) milling and sieving the granules Suitable liquids for granulation include water, ethanol and mixtures thereof. Water is a preferred granulation liquid.

The granules are dried to the desired moisture levels as described hereinbefore prior to their use in tablet formation or incorporation into a capsule for use as a unit dose.

Lubricant

Prior to tabletting the granules into composition, it is preferred that the granules are blended with a lubricant or glidant such that there is lubricant or glidant distributed over and between the granules during the compaction of the granules to form tablets.

Typically the optimum amount of lubricant required depends on the lubricant particle size and on the available surface area of the granules. Suitable lubricants include silica, talc, stearic acid, calcium or magnesium stearate and sodium stearyl fumarate and mixtures thereof. Lubricants are added to the granules in a finely divided form, typically 100% less than 150 micrometers and preferably 98% less than 38 micrometers, most preferably no particles greater than 40 micrometers in diameter (ensured typically by sieving). Lubricant surface area was typically 1-10 $m^2/g$, preferably from 6-10 $m^2/g$. The lubricant is suitably added to the granules at a level of from 0.1 to 1.0%, preferably from 0.1 to 0.4%, more preferably from 0.2 to 0.3% by weight of the granules. Lower levels can lead to sticking or jamming of the tablet die whereas higher levels may hinder tablet disintegration. Salts of fatty acids may be used as lubricants, such as calcium and/or magnesium stearate. A preferred lubricant is selected from the group consisting of magnesium stearate, sodium stearyl fumarate and mixtures thereof. It has been found that some lubricants, such as fatty acids, lead to pitting and loss of integrity in the coating layer of the tablets. It is thought that this may arise from partial melting of the lubricant as the coating layer is dried. Hence it is preferred that the lubricant has a melting point in excess of 55° C.

Tablets

Tablets for use in the present invention may be prepared by compressing granules, under high pressure, in order to form a tablet having the necessary crushing strength for the handling required during packaging and distribution. The use of granules formed from a granulated powder mixture improves flowability from storage hoppers to the tabletting press which in turn benefits the efficiency of tablet processing. The mixed metal compounds used in the tablets of the present invention typically have poor flowability properties at their desired particle size as detailed hereinbefore. Because it is desired that the tablets of the invention comprise high levels of mixed metal compound, of the order of 50% or more by weight of the tablet, the mixed metal compound must be formed into granules prior to tablet formation. A fine powder is apt to pack or "bridge" in the hopper, feed shoe or die, and thus tablets of even weight or even compression are not easily obtainable. Even if it were possible to compress fine powders to a satisfactory degree, air may be trapped and compressed, which may lead to splitting of the tablet on ejection. The use of granules helps to overcome these problems. Another benefit of granulation is the increase in bulk density of the final tablet when prepared from granules rather than from fine powder, reducing the size of the final tablet and improving the likelihood of patient compliance.

The tablets for use in the invention may be circular but are preferably generally bolus- or torpedo-shaped (also known as double convex oblong shaped tablet) i.e. having an elongate dimension, in order to assist swallowing of larger doses. Smaller tablet dose containing 250 mg of active were typically of circular shape, larger tablet dose containing 500 mg of active were typically of a bolus or torpedo-shaped. It may for example be in the form of a cylinder with rounded ends or elliptical in one dimension and circular in an orthogonal dimension, or elliptical in both. Some flattening of one or more parts of the overall shape is also possible.

Where the tablet is in the form of a tablet provided with a "belly-band", it is preferred if the width of the belly-band is 2 mm or more. It has been found that smaller belly-bands can lead to insufficient coverage or chipping or loss of integrity of the water-resistant coating of the tablet.

The tablets of the second aspect of the invention preferably have a hardness from 5 to 30 kgf as measured using a Holland C50 tablet hardness tester.

Water Resistant Coating

The tablets, once formed from granules, are preferably provided with a water-resistant coating.

The water-resistant coating may be applied to the tablet by any of the usual pharmaceutical coating processes and equipment. For example, tablets may be coated by fluid bed equipment (for example a "Wurster" type fluid bed dryer) coating pans (rotating, side vented, convention etc), with spray nozzles or guns or other sprayer types or by dipping and more recent techniques including Supercell tablet coater from Niro PharmaSystems. Variations in available equipment include size, shape, location of nozzles and air inlets and outlets, air flow patterns and degree of instrumentation. Heated air may be used to dry the sprayed tablets in a way that allows continuous spraying while the tablets are being simultaneously dried. Discontinuous or intermittent spraying may also be used, but generally requires longer coating cycles. The number and position of nozzles may be varied, as needed depending on the coating operation and the nozzle(s) is preferably aimed perpendicularly or nearly perpendicular to the bed although other direction(s) of aim may be employed if desired. A pan may be rotated at a speed selected from a plurality of operating speeds. Any suitable system capable of applying a coating composition to a tablet may be used. Virtually any tablet is acceptable herein as a tablet to be coated. The term "tablet" could include tablet, pellet or pill. Typically the preferred tablet will be in a form sufficiently stable physically and chemically to be effectively coated in a system which involves some movement of a tablet, as for example in a fluidized bed, such as in a fluidized bed dryer or a side vented coating pan, combinations thereof and the like. Tablets may be coated directly, i.e. without a subcoat to prepare the surface. Subcoats or topcoats may of course be used. If desired, the same or a similar coating application system can be employed for both a first or second or more coating applications. The coating composition is prepared according to the physical properties of its constituents, i.e. soluble materials are dissolved, insoluble materials are dispersed. The type of mixing used is also based on the properties of the ingredients. Low shear liquid mixing is used for soluble materials and high shear liquid mixing is used for insoluble materials. Usually the coating formulation consists of two parts, the colloidal polymer suspension and the pigment suspension or solution (e.g. red oxide or Quinoline yellow dye). These are prepared separately and mixed before use.

A wide range of coating materials may be used, for example, cellulose derivatives, polyvinylpyrrolidone, polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of methacrylate and tertiary amino alkyl methacrylate, copolymers of ethylacrylate methyl methacrylate and quaternary amino alkyl methacrylate and combinations of two or more hereof. Preferably, salts of methacrylate copolymers are used, e.g. butylated methacrylate copolymer (commercially available as Eudragit EPO).

The coating is suitably present as 0.05 to 10% by weight of the coated tablet, preferably from 0.5% to 7%. Preferably the coating material is used in combination with red iron oxide pigment ($Fe_2O_3$) (1% or more, preferably 2% or more by weight of the dried coating layer) which is dispersed throughout the coating material and provides an even colouring of the coating layer on the tablet giving a pleasant uniform appearance.

In addition to protecting the tablet core from moisture loss or ingress on storage, the water resistant coating layer also helps to prevent the rapid break-up of the tablet in the mouth, delaying this until the tablet reaches the stomach. With this purpose in mind, it is preferred if the coating material has low solubility in alkaline solution such as found in the mouth, but more soluble in neutral or acid solution. Preferred coating polymers are salts of methacrylate copolymers, particularly butylated methacrylate copolymer (commercially available as Eudragit EPO). Preferably the coating layer comprises at least 30% by weight of a coating polymer, more preferably at least 40% by weight.

The water loss or uptake of coated tablets is suitably measured as detailed hereinbefore for the measurement of the non-chemically bound water content for granules. From a set of freshly prepared coated tablets, some are measured for non-chemically bound water immediately following preparation, and others are measured after storage as detailed above.

Capsules

Suitable capsules for use in the second aspect of the invention are hard gelatine capsules, although other suitable capsule films may be used.

Use of Unit Doses

Amounts of from 0.1 to 500, preferably from 1 to 200, mg/kg patient body weight of mixed metal compound are preferably administered daily to obtain the desired results. Nevertheless, it may be necessary from time to time to depart from the amounts mentioned above, depending on the body weight of the patient, the animal species of the patient and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses. Ultimately, the dose will depend upon the discretion of the attendant physician but may also be suitable for self-medication. Administration before meals, e.g. within one hour before a meal is suitable. Alternatively, the dose may be taken with a meal or after a meal.

A typical tablet of the invention for human adult administration may comprise from 1 mg to 5 g, preferably from 10 mg to 2 g, more preferably from 100 mg to 1 g, such as from 150 mg to 750 mg, from 200 mg to 750 mg or from 250 mg to 750 mg of mixed metal compound.

Preferably the unit doses of the invention comprise at least 100 mg of mixed metal compound. Preferably the unit doses of the invention comprise at least 120 mg of mixed metal compound. Preferably the unit doses of the invention comprise at least 150 mg of mixed metal compound. Preferably the unit doses of the invention comprise at least 200 mg of mixed metal compound. Preferably the unit doses comprise at least 250 mg of a mixed metal compound. Preferably the unit doses comprise at least 300 mg of a mixed metal compound. A more preferred unit dose comprises 500 mg of mixed metal compound. The preferred unit dose weight is less than 750 mg, more preferably less than 700 mg, to aid with patient compliance for oral dosage. A particularly preferred unit dose contains 200 mg (±20 mg) of a mixed metal compound. A particularly preferred unit dose contains 250 mg (±20 mg) of a mixed metal compound. A particularly preferred unit dose contains 300 mg (±20 mg) of a mixed metal compound. When the unit dose is a tablet, the preferred unit dose weight includes any optional coating.

The tablet forms may be packaged together in a container or presented in foil strips, blister packs or the like, e.g. marked with days of the week against respective doses, for patient guidance.

Metals and Anions

As discussed, the at least one trivalent metal selected from iron (III) and aluminium and the at least one divalent metal selected from of magnesium, iron, zinc, calcium, lanthanum and cerium.

In one preferred aspect the divalent metal is at least one of magnesium, iron, zinc, and calcium.

In one preferred aspect the divalent metal is at least one of iron, zinc, and calcium.

In one preferred aspect the divalent metal is at least one of magnesium, zinc, and calcium.

In one preferred aspect the divalent metal is at least one of magnesium, iron and calcium.

In one preferred aspect the divalent metal is at least one of magnesium, iron and zinc.

In one preferred aspect the divalent metal is at least one of magnesium and calcium.

In one preferred aspect the divalent metal is at least one of magnesium and iron.

In one preferred aspect the divalent metal is at least one of magnesium and zinc.

In one preferred aspect the divalent metal is at least one of iron and zinc.

In one preferred aspect the divalent metal is at least one of iron and calcium.

In one preferred aspect the divalent metal is at least one of zinc and calcium.

In one preferred aspect the trivalent metal is at least iron (III). In one preferred aspect the trivalent metal is solely iron (III).

In one preferred aspect the divalent metal is at least magnesium. In one preferred aspect the divalent metal is solely magnesium.

In formula (I) the value of a is preferably from 0.2 to 0.4. If a is above 0.4 than the antacid activity will decrease because of a lower amount of the $MgOH_2$ sheets. If a is above 0.4 or less than 0.2 the mixed metal may also collapse into a mixture of single metal compounds. If a is below 0.2 the amount of $MgOH_2$ may be too high and increase the occurrence of a laxative effect. If a is above 0.4 or less than 0.2 the compounds may not buffer to the optimum pH range of between pH 3-4.5.

Commercially available cream of magnesia tablets contain approximately 280 g magnesium/kg tablet weight whereas mixed metal compound 2 contains approximately 136 g magnesium/kg tablet weight.

In formula (III) the value of x is preferably from 0.2 to 0.4 for the same reasons as provided above for a in formula (I)

In one preferred aspect the mixed metal compound contains at least one of hydroxyl and carbonate anions.

The divalent metal and/or $M^{II}$ of formulae (I), (II) and (III) is preferably selected from Mg(II), Zn(II), Fe(II), Cu(II), Ca(II), La(II) and Ni(II). Of these, Mg is especially preferred.

The trivalent metal and/or $M^{III}$ of formulae (I), (II) and (III) is preferably selected from Mn(III), Fe(III), La(III), Al(III) Ni(III) and Ce(III). Of these, Fe(III) and Al(III) are preferred and Fe(III) is especially preferred. Herein, (II) means a metal in a divalent state and (III) means a metal in a trivalent state.

$A^{n-}$ is preferably selected from one or more of carbonate, hydroxycarbonate, oxo-anions (e.g. nitrates, sulphate), metal-complex anion (e.g. ferrocyanide), polyoxo-metalates, organic anions, halide, hydroxide and mixtures thereof. Of these, carbonate is especially preferred.

Preferably, the compound comprises less than 200 g/kg of aluminium, more preferably less than 100 g/kg, even more preferably less than 50 g/kg expressed as weight of aluminium metal per weight of compound.

More preferably, only low levels of aluminium are present such as less than 10 g/kg, preferably less than 5 g/kg.

Even more preferably, the compound is free from aluminium (Al). By the term "free from aluminium" it is meant that the material termed "free from aluminium" comprises less than 1 g/kg, more preferably less than 500 mg/kg, even more preferably less than 200 mg/kg, most preferably less than 120 mg/kg expressed as weight of elemental aluminium per weight of compound.

Suitably the compound contains iron(III) and at least one of magnesium, iron, zinc, calcium, lanthanum or cerium, more preferably at least one of magnesium, lanthanum or cerium, most preferably magnesium.

Preferably, the compound comprises less than 100 g/kg of calcium, more preferably less than 50 g/kg, even more preferably less than 25 g/kg expressed as weight of elemental calcium per weight of compound.

More preferably, only low levels of calcium are present such as less than 10 g/kg, preferably less than 5 g/kg.

Even more preferably, the compound is free from calcium. By the term "free from calcium" it is meant that the material termed "free from calcium" comprises less than 1 g/kg, more preferably less than 500 mg/kg, even more preferably less than 200 mg/kg, most preferably less than 120 mg/kg expressed as weight of elemental calcium per weight of material.

Typically, regular doses of antacids with high levels of carbonate such as $CaCO_3$ or $MgCO_3$ provide high levels of carbonate (respectively 600 g/kg and 710 g/kg) which may cause alkalosis. Whereas the present mixed metal compounds provide less than 100 g/kg. Preferably carbonate is present in the present compound in amounts of less than 600 g/kg, more preferred less than 200 g/kg, even more preferred less than 100 g/kg. Material of compound (II) obtained by heat-treatment of compound (I) typically contains a lower amount of carbonate.

Preferably, the compound is free from calcium and free from aluminium.

The final unit dose, comprising granules and any other material making up the final unit dose, as a whole, is also preferably free from aluminium and/or preferably free from calcium, using the definitions as detailed above.

Preferably the mixed metal compound comprises at least some material which is a Layered Double Hydroxide (LDH). More preferably, the mixed metal compound of formula (I) is a layered double hydroxide. As used herein, the term "Layered Double Hydroxide" is used to designate synthetic or natural lamellar hydroxides with two different kinds of metallic cations in the main layers and interlayer domains containing anionic species. This wide family of compounds is sometimes also referred to as anionic clays, by comparison with the more usual cationic clays whose interlamellar domains contain cationic species. LDHs have also been reported as hydrotalcite-like compounds by reference to one of the polytypes of the corresponding [Mg—Al] based mineral.

A particularly preferred mixed metal compound contains at least one of carbonate ions, and hydroxyl ions.

A particularly preferred compound contains as $M^{II}$ and $M^{III}$, magnesium and iron (III) respectively.

The mixed metal compound or compounds may be suitably made by co-precipitation from a solution, e.g. as described in WO 99/15189, followed by centrifugation or filtration, then drying, milling and/or sieving. The mixed metal compound is then rewetted again as part of the wet-granulation process and the resulting granules dried in a fluid-bed. The degree of drying in the fluid-bed is used to establish the desired water content of the final tablet.

Two methods of coprecipitation may be used namely one at low supersaturation whereby the pH of the reaction solution is maintained constant by controlling the addition of a second solution of an alkali or alternatively precipitation at high supersaturation whereby the pH of the reaction solution is continuously changed by addition of the mixed metal solution to the a solution alkali already present in the reactor vessel. The precipitation whereby the pH is kept constant is preferred as this avoids the formation of single metal compounds such as $M(OH)_2$ and/or $M(OH)_3$ phases instead of mixed metal compound.

Other preparation methods of the mixed metal compound are also possible: e.g. a method involving separate nucleation and aging steps as reported by Zhao et al (Zhao Y, et al. (2002) Chem Mater 14: 4286 or a urea hydrolysis, induced hydrolysis method, salt-oxide, sol-gel, electrosynthesis, in situ oxidation of MII, "Chimie Douce" method or alternatively, mixed metal compound may be formed by heating an intimate mixture of finely divided single metal salts at a temperature whereby solid-solid reaction can occur, leading to mixed metal compound formation.

Furthermore different post synthesis heat-treatment steps e.g. hydrothermal, microwave, ultrasound may be used after precipitation of the mixed metal compound to facilitate the ageing process of the mixed metal compound in order to prepare a well-crystallised phase although no ageing is preferred to maintain a small crystallite size. In addition, variations of methods for the separation to mixed metal compound from the reactive medium is possible or washing Additionally, different drying or milling processes may be used to treat the final product.

The mixed metal compound of formula (II) may be calcined by heating at temperatures in excess of 200° C. in order to decrease the value of z in the formula and to decrease the amount of carbonate. In this case, it may be necessary to add water after calcination and prior to incorporation of the mixed metal compound in the granules in order to achieve the desired non-chemically bound water content of the granules.

It will be appreciated by those skilled in the art that the water provided by $zH_2O$ in formula (I) may provide part of the 3 to 12% by weight of non-chemically bound water (based on the weight of the granular material). One skilled in the art may readily determine the value of z based on standard chemical techniques. Once the material of the present invention has been provided the amount of the non-chemically bound water may then also be readily determined in accordance with the procedure described herein.

By mixed metal compound, it is meant that the atomic structure of the compound includes the cations of at least two different metals distributed uniformly throughout its structure. The term mixed metal compound does not include mixtures of crystals of two salts, where each crystal type only includes one metal cation. Mixed metal compounds are typically the result of coprecipitation from solution of different single metal compounds in contrast to a simple solid physical mixture of 2 different single metal salts. Mixed metal compounds as used herein include compounds of the same metal type but with the metal in two different valence states e.g. Fe(II) and Fe(III) as well as compounds containing more than 2 different metal types in one compound.

The mixed metal compound may also comprise amorphous (non-crystalline) material. By the term amorphous it is meant that the material has either crystalline phases which have crystallite sizes below the detection limits of x-ray diffraction techniques, or crystalline phases which have some degree of ordering, but which do not exhibit a crystalline diffraction pattern and/or true amorphous materials which exhibit short range order, but no long-range order.

The compound of formula (II) is preferably formed with (i) no aging of the slurry (e.g. no heat applied nor is the reaction precipitate slurry held prior to washing and isolation) (ii) or hydrothermal treatment to avoid the crystals of the compound growing in size and to maintain a high surface area facilitating the release of hydroxide ions (OH⁻). The unaged compound of formula (II) is also preferably maintained in a fine particle size form during the post-synthesis route to maintain good activity (but not too fine to avoid flowability problems).

To increase flowability of the compound of formula (I) or (II) typically larger particles are preferred however this in turn reduces the available surface area and decreases the buffering ability. We have however found that by avoiding ageing of the reaction slurry of compound of formula II (thereby maintaining a small crystallite size) and instead increasing the particle size of the compound of formula (I) or (II) only during the wet-granulation process (by mixing the compound of formula (I) or (II) with preferred excipients and granulating within a preferred particle size range) the antacid properties are maintained as well as avoiding flowability problems typically associated with these powders during the tabletting process.

Further Aspects

In one highly aspect of the present invention:
the mixed metal compound contains iron (III) and magnesium, and is provided in the form of a granular material comprising
(i) at least 50% by weight, based on the weight of the granular material, of the mixed metal compound
(ii) from 3 to 12% by weight, based on the weight of the granular material, of non-chemically bound water, and
(iii) no greater than 47% by weight based on the weight of the granular material of excipient.

In a further highly aspect of the present invention:
the mixed metal compound is of formula (I):

$$M^{II}_{1-a}M^{III}_{a}O_{b}A^{n-}_{c}\cdot zH_2O \qquad (I)$$

where is magnesium;
$M^{III}$ is iron (III);
$A^{n-}$ is at least one n-valent anion;

$$2+a=2b+\Sigma cn,$$

$\Sigma cn < 0.9a$, and
z is 2 or less.

Diseases

As discussed herein the mixed metal compound is used for neutralising or buffering stomach acid. It will be understood by one skilled in the art that such action may be utilised in the prevention or treatment of peptic ulcers, heartburn, acid indigestion, acid reflux, dyspepsia, gastritis, Zollinger-Ellison syndrome or combinations thereof. The present invention is particularly useful in the prevention or treatment of peptic ulcers.

The present invention will now be described in further detail by way of example only with reference to the accompanying figures in which:—

FIG. 1 shows the gastric pH profile in the presence of food and antacids.

EXAMPLES

Compound 1

Formed by the reaction of aqueous solutions of magnesium sulphate and ferric sulphate in the presence of sodium hydroxide and sodium carbonate. The synthesis reaction can be described by:
$4MgSO_4+Fe_2(SO_4)_3+12NaOH+XS$ $Na_2CO_3 \rightarrow Mg_4Fe_2(OH)_{12}\cdot CO_3\cdot nH_2O+7Na_2SO_4+(XS-1)Na_2CO_3$. An excess (XS) sodium carbonate was used. The co-precipitation was carried out at approximately pH 10 at ambient temperature (15-25° C.) as described in WO 99/15189 Example 3, Method 1 with no ageing (no ageing is defined here as no additional heat-treatment step of the reaction slurry to prevent further growth of crystal size and thereby maintain high surface area of crystals). The resulting precipitate was filtered, washed, dried, milled and then sieved such that all material is less than 106 micron. The co-precipitation was carried out to target a Mg:Fe ratio of 2:1 and a nominal formula of $Mg_4Fe_2(OH)_{12}\cdot CO_3\cdot 4.6H_2O$. This formula can also be expressed in the oxide form as $4MgO\cdot Fe_2O_3\cdot CO_2\cdot 10.6H_2O$ which would be expected to give elemental values by XRF (X-ray Fluorescence Spectrophotometry) of MgO=28.3% wt/wt, $Fe_2O_3$=28.7% which gives a Mg:Fe mole ratio=1.9:1. The actual molecular formula found by analysis was: $[Mg_{3.8}Fe_2(OH)_{11.8}][0.72(CO_3)0.16(SO_4).4.3H_2O]$ because of the presence of a small amount of sulphate in the material. Carbon content of the compound was determined by standard LECO (carbon analyser) and expressed as $CO_2$ or $CO_3$. The sulphate content was determined by XRF. The water content in the oxide formula was determined by: $H_2O=100\%-(MgO+Fe_2O_3+SO_3+CO_2)$. XRD showed that the mixed metal compound was characterized by the presence of the poorly crystalline hydrotalcite type structure and had a diffraction line half width of 0.67 deg 2theta which equates to a crystallite size of 150 Å. The amount of non-chemically bound water is determined by drying to constant weight at 105° C. in an oven and was 7.3% wt/wt. The sodium content (expressed as $Na_2O$) was less than 0.05% wt/wt.

Compound 2

A dry blend was prepared of 79.75% of the sieved powder from compound 1 mixed with 15% pregelatinised starch, 5% micronised crospovidone and 0.25% magnesium stearate (this magnesium stearate was kept separately for addition to the dried granules). The dry blends were mixed in a mixer granulator. The powder mix is then granulated with sufficient water to produce the granulate which is then transferred to a fluid-bed dryer for drying to a target moisture content of 5-7% w/w. The granules are then milled with a high speed blade mill until it passed through a 425 micron aperture sieve. The sieved granule was then blended with 0.25% w/w of pre-sieved magnesium stearate (also sieved through a 0.425 mm aperture mesh) to produce the tablet blend (the magnesium stearate was blended with the granules immediately after sieving of magnesium stearate). This tablet blend was then compressed on a Manesty F3 single station press using a double convex oblong punch and die set into tablets of typical hardness from 10 to 20 kgF as measured by a Holland C50 tablet hardness tester. This tablet contained 500 mg of the active ingredient with a nominal composition of $Mg_4Fe_2(OH)_{12}.CO_3.4.6H_2O$ as determined from the MgO content (by XRF) of the tablet. XRD showed that the granules contained the mixed metal compound characterized by the presence of the poorly crystalline hydrotalcite type structure. The amount of non-chemically bound water of the tablet is determined by using a Satorius MA30 infra-red balance set at 75° C. with automatic endpoint determination and was 5% wt/wt.

Compound 3

The powder (of compound 1 sieved to less then 106 micron) was heat-treated at 500° C. for a duration of 30 minutes in accordance with WO-A-2006/085079. The amount of non-chemically bound water is determined by drying to constant weight at 105° C. in an oven and was 1.1% wt/wt. XRF analysis of the heat-treated samples measured values of MgO=45% wt/wt, $Fe_2O_3$=47% which gives a Mg:Fe mole ratio=1.9:1.

Compound 4

Prepared as described for compound 1 but for a molar ratio of Mg:Fe of 3:1.

Compound 5

The powder of compound 4 (sieved to less than 106 micron) was heat-treated at 500° C. for a duration of 30 minutes in accordance with PCT/GB2006/000452.

Compound 6

Formed by the reaction of aqueous solutions of magnesium sulphate and aluminium sulphate in the presence of sodium hydroxide and sodium carbonate. The synthesis reaction can be described by:

$6MgSO_4+Al_2(SO_4)_3.14H_2O+16NaOH+XS\ Na_2CO_3 \rightarrow [Mg_6Al_2(OH)_{16}CO_3.4H_2O]+9Na_2SO_4+(XS-1)Na_2CO_3+10H_2O$. An excess (XS) sodium carbonate was used. The co-precipitation was carried out between pH 9.5-10 at ambient temperature (15-25° C.). Solution A consisted of the metal salts and solution B consisted of sodium hydroxide and carbonate. The molar ratio between the NaOH and $Na_2CO_3$ in solution B was 4.3:1. Both solutions were added together over 45 minutes by use of peristaltic pumps which were kept at 6.9 rpm for solution A and 5.6 rpm for solution B. The addition speed of solution B was varied to maintain the pH in the range of 9.5-10. The resulting slurry was not aged (no ageing is defined by filtering the slurry immediately with no additional steps such as heat treatment; this ensured that crystal sizes were kept small). The resulting precipitate was filtered, washed, dried and then sieved to a particle size of less than 106 micron. The resulting product formula was $[Mg_6Al_2(OH)_{16}CO_3.4H_2O]$. The product had a XRF composition of MgO=15% wt/wt and $Al_2O_3$=26% wt/wt, Mg:Al molar ratio of 2.9:1. XRD showed that the compound was of hydrotalcite type structure.

Compound 7

The powder of compound 6 was granulated and compressed into a tablet according to method described for compound 2. The tablet contained 500 mg of the active ingredient $[Mg_6Al_2(OH)_{16}CO_3.4H_2O]$ as determined from the MgO content (by XRF) of the tablet.

Compound 8

Compound 2 but with coating prepared by the following: Coating of the tablets was achieved using a hand held spray gun with 300-400 tablet cores placed in a rotating basket with the hot air for drying the tablets supplied by a hot air gun. The coating suspension was applied at a sufficient rate to ensure adherence to the tablet core but low enough to prevent tablet core disintegration during the coating process. The coating suspension comprised: 84% purified water, 0.8% sodium dodecyl sulphate, 8.08% butylated methacrylate copolymer (Eudragit EPO), 1.21% stearic acid, 2.09% talc, 2.83% Mgstearate, 0.64% titanium dioxide, 0.32% red iron oxide. The coating was dried after application using hot air at 40° C. The Eudragit EPO film coating is applied to approximately 4.5% (W/W) to provide even coverage. The disintegration time of the coated tablets was measured using a disintegration bath Copley DTG 2000 IS and found to be less than 30 minutes in both water or acid. This tablet contained 500 mg of the active ingredient with a nominal composition of $Mg_4Fe_2(OH)_{12}.CO_3.4.6H_2O$ as determined from the MgO content (by XRF) of the tablet. The amount of non-chemically bound water of the tablet is determined by using a Satorius MA30 infra-red balance set at 75° C. with automatic endpoint determination and was 6% wt/wt.

Compound 9

Compound 7 but with coating prepared by the following: Coating of the tablets was achieved using a hand held spray gun with 300-400 tablet cores placed in a rotating basket with the hot air for drying the tablets supplied by a hot air gun. The coating suspension was applied at a sufficient rate to ensure adherence to the tablet core but low enough to prevent tablet core disintegration during the coating process.

The coating suspension comprised: 84% purified water, 0.8% sodium dodecyl sulphate, 8.08% butylated methacrylate copolymer (Eudragit EPO), 1.21% stearic acid, 2.09% talc, 2.83% Mgstearate, 0.64% titanium dioxide, 0.32% yellow oxide. The coating was dried after application using hot air at 40° C. The Eudragit EPO film coating is applied to approximately 4.5% (W/W) to provide even coverage. The disintegration time of the coated tablets was measured using a disintegration bath Copley DTG 2000 IS and found to be less than 30 minutes in both water or acid.

This tablet contained 500 mg of the active ingredient with a nominal composition of $Mg_6Al_2(OH)_{12}.CO_3.4.6H_2O$ as determined from the MgO content (by XRF) of the tablet.

Compound 10

Tablet core prepared as described for compound 2 but with milling of granules with a high speed rotating element to provide granules that passed through a 1000 micron aperture sieve. The tablet core was then coated as the coating method described for compound 8. This tablet contained 500 mg of the active ingredient with a nominal composition of $Mg_4Fe_2(OH)_{12}.CO_3.4.6H_2O$ as determined from the MgO content (by XRF) of the tablet.

Compound 11

Compound 6 was sieved to less than 106 micron and heat treated at 500° C. for 30 minutes.

Compound 12

Compound 6 was sieved to less than 106 micron and heat treated at 750° C. for 30 minutes.

Macrosorb™

A hydrotalcite of the formula $Al_2Mg_6(OH)_{16}CO_3.4H_2O$ commercially available from Ineos Silicas.

Altacite Plus

Altacite, a hydrotalcite of the same formula as Macrosorb™ commercially available in the form of an aqueous slurry.

Rennie™, Alucap™, Talcid™, Ultacit™, Talidat™ and Cream of Magnesia (Boots)

All commercially available compounds

Method 1

Acid Neutralization Capacity (ANC) was measured by the following:

The test compound was added to a beaker containing 70 ml of analar water kept at 37° C. using a Grant OLS200 orbital shaker. The temperature of the solution was maintained at 37±3° C. for the duration of the experiment. 30 ml of 1.0N hydrochloric acid was then added into the test preparation while continuing to stir with the magnetic stirrer. The solution was stirred for 15 minutes, accurately timed. The solution was then titrated immediately, and in a period not to exceed an additional 5 minutes, with 0.5N sodium hydroxide to attain a stable (for 10 to 15 seconds) of pH of 3.5. A 718 Stat Titrino was used for the titration. Each compound was analysed in triplicate. Tablets intended to be taken by first chewing were first crushed by mortar and pestle to simulate the chewing process. This method follows the USP (US Pharmacopeia) general chapter 301. The formula for $mEq/g=(30 \times N_{HCl})-(V_{NaOH} \times N_{NaOH})/g$ substance tested.

Method 2

To measure the highest pH attained during acid addition, 100 ml of water was heated in a beaker to 37° C. using a Grant OLS200 orbital shaker rotating at 170 rpm. The water was pre-titrated to pH 4 by addition of 0.1N HCl acid. The test compound was added to the solution, then using a Metrom Stat Titrino 718 0.1N HCl acid was added at a rate of 3 mls per second. The pH and temperature was measured every 30 seconds for a total of 1800 seconds. The highest pH value achieved during this time was recorded. pH values were measured using a typical pH meter; model Jenway 3520 pH meter with VWR 6621759 electrode. The pH meter was calibrated with buffers before any measurement at room temperature (25° C.).

This method is an indicator for the occurrence of the acid-rebound effect. This is associated with antacids with a too rapid onset of action whereby the pH is suddenly increased to a pH above 5 during the antacid activity i.e. a pH below 5 is preferred (but pH should also not drop too a very low pH value i.e. less than 2 as this would indicate that the antacid is not working).

Method 3 pH buffering in the presence of food was determined in an in vitro gastrointestinal tract model.

In repeat experiments (N=3 or 4), a control (no antacid), one Alucap capsule (475 mg active ingredient content), one tablet of compound 8, 500 mg of compound 1 (dosed as 2 gelatine capsules), 500 mg powder of compound 3 (dosed as 2 gelatine capsules) were mixed in separate experiments with a standard FDA meal (meal designed according to the guidelines of the US Food and Drugs Administration FDA typically used for bioavailability studies to provide the greatest effects on gastrointestinal physiology). Compound 1 and 3 were dosed in the form of gelatine capsules each filled with 250 mg of powder of the antacid. Experiments were performed in Tiny-TIM (Nederlandse Organisatie voor Toegepast-Natuurwetenschappelijk Onderzoek TNO, Zeist, The Netherlands). Details of this model have been widely published; for example as in U.S. Pat. No. 5,525,305. These experiments were performed under the average physiological conditions of the gastrointestinal tract representative for humans. These conditions include the dynamics of gastric emptying and intestinal transit times, the gastric and the intestinal pH values, and the composition and activity of the secretion products. The pH in the gastric compartment was measured during 300 minutes (FIG. 1).

The conclusion from this graph is the following:
the preferred compounds buffer the pH for up to a period of approximately 2 hours (in comparison to the control-food only). In this model the gastric emptying is approx 80% at 2 hours, approximately 95% at 3 hours and 100% at 6 hours. Therefore, this demonstrates that the preferred antacid has a long duration of action ie antacid activity is provided until approximate 80% of the stomach is emptied.

the preferred compounds buffer in the presence of food. In contrast a commercially available antacid based on AlOH$_3$ does not appear to provide buffering in the presence of food.

the stomach pH does not suddenly change to (or exceed a pH of 7) in the presence of food and thereby avoids acid rebound effect or irreversible inactivation of pepsin.

Method 4

Tablet volume was determined by placing 5 tablets in a measuring cylinder containing 50 ml of water. The volume displacement was determined by measuring the change in water volume before and after placing the 5 tablets in the measuring cylinder. The volume for each tablet was then calculated by: volume displacement/5. The change in volume was measured immediately after placing the tablets in the measuring cylinder i.e. before the tablets disintegrated in water.

The preferred MgFe or MgAl tablets do not need to be dosed in crushed form to achieve good ANC 1 values.

There is no significant difference between administration of a crushed tablet or a whole tablet of our preferred MgFe or MgAl compounds. This may be an advantage for patients in providing more consistent antacid properties (i.e. performance will be less dependent on how or whether a tablet is chewed.

heat-treating MgFe or MgAl hydrotalcites increases antacid properties preferred temperature for heat-treatment is between 200 and 500 Celsius, temperatures at 750 or higher result in lower ANC 1 values antacid properties increase with HT ratio

TABLE 1

Acid neutralization capacity (ANC)

| Active Ingredient (HT = hydrotalcite or mixed metal compound) | Name Dose-form | Dose-form administered in test | Method 1 - ANC (mEq/g active ingredient) |
|---|---|---|---|
| Control | | | 0.1 |
| MgFe 2:1 HT | Compound 1 | dosed as 500 mg powder | 14.4 |
| MgFe 2:1 HT | Compound 2 | dosed by crushing one uncoated tablet | 15.1 |
| MgFe 2:1 HT | Compound 2 | dosed as one uncoated tablet | 16.0 |
| MgFe 2:1 HT | Compound 8 | dosed as one coated tablet | 16.8 |
| MgFe 2:1 HT | Compound 10 (consisting of larger granules) | dosed as one coated tablet, | 15.3 |
| MgFe 2:1 HT-heat-treated | Compound 3 | dosed as 500 mg powder | 22.0 |
| MgFe 3:1 HT | Compound 4 | dosed as 500 mg powder | 16.9 |
| MgFe 3:1 HT-heat-treated | Compound 5 | dosed as 500 mg powder | 23.8 |
| MgAl 3:1 HT | Compound 6 | dosed as 500 mg powder | 23.2 |
| MgAl 3:1 HT | Compound 7 | dosed as one crushed uncoated tablet | 23.8 |
| MgAl 3:1 HT | Compound 7 | dosed as one uncoated tablet | 24.1 |
| MgAl 3:1 HT | Compound 9 | dosed as one coated tablet | 23.6 |
| MgAl 3:1 HT-heat-treated | Compound 11 | dosed as 500 mg powder | 23.5 |
| MgAl 3:1 HT-heat-treated | Compound 12 | dosed as 500 mg powder | 18.8 |
| MgAl 3:1 HT | Macrosorb | dosed as 500 mg powder | 25.2 |
| MgAl 3:1 HT | Altacite Plus ™ | dosed as 5 ml suspension | 22.4 |
| MgAl 3:1 HT | Talcid ™ | dosed as one crushed tablet | 29.1 |
| MgAl 3:1 HT | Talcid ™ | dosed as 5 ml suspension | 28.0 |
| MgAl 3:1 HT | Ultacit ™ | dosed as one crushed tablet | 22.4 |
| MgAl 3:1 HT | Talidat ™ | one pastille | 22.5 |
| CaCarbonate | Rennie ™ | two crushed tablets | 12.4 |
| Al(OH)$_3$ | Alucap ™ | one capsule (475 mg active) | 14.1 |
| Mg(OH)$_2$ | Cream of Magnesia | two tablets (of 300 mg Mg(OH)$_2$) | 31.2 |
| Mg(OH)$_2$ | Cream of Magnesia | one tablet (300 mg) | 33.3 |

Conclusions from this table:

MgFe HT has antacid properties comparable to those of currently commercially available compounds (i.e. Rennie)

MgAl HT has better antacid properties to the MgFe HT but the MgFe HT has the advantage of being Al-free Antacids based on HT are currently only available as chewable tablets or in a liquid dose form

TABLE 2

Results obtained by method 2

| active ingredient | name | dose-form administered in test | Method 2 highest pH achieved during acid addition |
|---|---|---|---|
| control | — | — | |
| MgFe 2:1 HT | Compound 1 | dosed as 500 mg powder | |
| MgFe 2:1 HT | Compound 2 | dosed as one crushed tablet | 3.3 |
| MgFe 2:1 HT | Compound 2 | 500 mg powder | 4.5 |
| MgFe 2:1 HT-heat-treated | Compound 3 | 500 mg powder | 3.1 |
| MgAl 3:1 HT | Compound 6 | dosed as one crushed tablet | 3.7 |
| MgAl 3:1 HT | Macrosorb | 500 mg powder | 5.9 |
| MgAl 3:1 HT | Altacite Plus ™ | 10 ml suspension | 6.6 |
| CaCarbonate | Rennie ™ | two crushed tablets | 9.0 |
| Al(OH)$_3$ | Alucap ™ | one capsule | 5.2 |
| Mg(OH)$_2$ | Cream of Magnesia | two tablets (of 300 mg Mg(OH)$_2$) | 4.3 |

Conclusions from this table
Data shows the advantage of using our preferred compounds to avoid the stomach pH rising above pH 5 and avoid acid-rebound effect ie compounds that buffer to the optimum pH range of between pH 3-4.5.

TABLE 3

Dose-efficacy

| | Dose-form | Method of administration in test method 1 | Tablet Size (volume) Method 5 cm$^3$ | Tablet Weight g | Mixed metal compound (Hydrotalcite) per tablet mg | Mixed metal compound (Hydrotalcite) per tablet % | ANC (Method 1) per tablet weight |
|---|---|---|---|---|---|---|---|
| MgAl 3:1 HT | Ultacite | Chewable Tablet | One crushed tablet | 0.83 | 1.04 | 500 | 48 | 26.21 |
| MgAl 3:1 HT | Talidat | Pastille | Pastille | 1.00 | 1.58 | 500 | 32 | 17.06 |
| MgAl 3:1 HT | Talcid | Chewable Tablet | One crushed tablet | 0.66 | 1.00 | 500 | 50 | 29.09 |
| MgAl 3:1 HT | Compound 7 | Tablet | One tablet (not crushed) | 0.50 | 0.73 | 500 | 68 | 32.48 |
| MgAl 3:1 HT | Compound 9 | Tablet | One tablet (not crushed) | 0.50 | 0.77 | 500 | 65 | 30.62 |
| MgFe 2:1 HT | Compound 2 | Tablet | One tablet (not crushed) | 0.60 | 0.66 | 500 | 76 | 22.79 |
| MgFe 2:1 HT | Compound 8 | Tablet | One tablet (not crushed) | 0.60 | 0.69 | 500 | 72 | 22.18 |

Conclusions from this table:
The preferred tablet formulations containing MgAl or MgFe mixed metal compounds do not necessarily require chewing to achieve similar ANC values to those currently commercially available.
The preferred tablet formulations are more weight-effective, lighter and smaller tablets and have similar ANC values to those commercially available.
The preferred tablet formulations contain more than 50% hydrotalcite in contrast to those commercially available

REFERENCES

1) Synthesis and antacid property of Mg—Fe layered double hydroxide. Hirahara, Hidetoshi; Sawai, Yoshiyuki; Aisawa, Sumio; Takahashi, Satoshi; Umetsu, Yoshio; Narita, Eiichi. Department of Chemical Engineering, Faculty of Engineering, Iwate University, Morioka, Japan. Nendo Kagaku (2002), 42(2), 70-76.
2) IN-A1-192168
3) Acid neutralization and bile acid binding capacity of hydrotalcite compared with other antacids: an in vitro study. Miederer, S.-E.; Wirtz, M.; Fladung, B. Department of Internal Medicine, Gastroenterology and Metabolism, University of Bonn, University of Bielefeld, Leverkusen, Germany. Chinese Journal of Digestive Diseases (2003), 4(3), 140-146.
4) Evaluation of buffering capacity and acid neutralizing-pH time profile of antacids. Lin, Mei-Shu; Sun, Pin; Yu, Hsiu-Ying. School of Pharmacy, College of Medicine, National Taiwan University, Taipei, Taiwan. Journal of the Formosan Medical Association (1998), 97(10), 704-710.
5) JP-A-10236960
6) Interaction of an aluminum-magnesium-containing antacid and gastric mucus: possible contribution to the cytoprotective function of antacids. Grubel, P.; Bhaskar, K. R.; Cave, D. R.; Garik, P.; Stanley, H. E.; Lamont, J. T. Division of Gastroenterology, St. Elizabeth's Medical Center of Boston, Harvard Medical School, Boston University, Boston, Mass., USA. Alimentary Pharmacology and Therapeutics (1997), 11(1), 139-145

7) EP-A-0638313
8) Antacid activity of calcium carbonate and hydrotalcite tablets: Comparison between in vitro evaluation using the "artificial stomach-duodenum" model and in vivo pH-metry in healthy volunteers. Vatier, J.; Ramdani, A.; Vitre, M. T.; Mignon, M. Cent. Hospitalier Univ. X. Bichat, Paris, Fr. Arzneimittel-Forschung (1994), 44(4), 514-18.
9) ES-A-2018952
10) CA-A-1198674
11) DE-A-3346943
12) The in vitro antacid and anti-pepsin activity of hydrotalcite. Playle A. C., Gunning S. R. and Llewellyn. Pharm. Acta Helv. 49, Nr. 9/10 (1974)
13) Acid neutralization capacity of Canadian antacid formulations. Can Med Assoc J. Vol. 132, Mar. 1, 1985, pp 523-527
14) U.S. Pat. No. 3,650,704

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A method of treating a disease characterized by elevated levels of stomach acid in a subject, comprising administering a therapeutically effective amount of a mixed metal compound to said subject, wherein the mixed metal compound comprises:
   at least one trivalent metal selected from the group consisting of iron (III) and aluminum; and
   at least one divalent metal selected from the group consisting of magnesium, iron, zinc, calcium, lanthanum, and cerium,
   wherein
   (A) the mixed metal compound is of formula (I):

$$M^{II}_{1-a}M^{III}_{a}O_{b}A^{n-}_{c} \cdot zH_2O \quad (I)$$

where $M^{II}$ is the at least one divalent metal;
   $M^{III}$ is the at least one trivalent metal;
   $A^{n-}$ is at least one n-valent anion;

$2+a=2b+\Sigma cn$;

$\Sigma cn < 0.9a$; and
   z is 2 or less.

2. The method according to claim 1 wherein in formula (I) z is 1.8 or less.
3. The method according to claim 1 wherein in formula (I) z is 1.5 or less.
4. The method according to claim 1 wherein in formula (I) a is from 0.1 to 0.4.
5. The method according to claim 1 wherein in formula (I) a is from 0.2 to 0.4.
6. The method according to claim 1 wherein in formula (I) a is from 0.2 to 0.34.
7. The method according to claim 1 wherein in formula (I) a is <0.3.
8. The method according to claim 1 wherein in formula (I) b is 1.5 or less.
9. The method according to claim 1 wherein in formula (I) b is 1.2 or less.
10. The method according to claim 1 wherein in formula (I) $0.03a < \Sigma cn < 0.7a$.
11. The method according to claim 1 wherein in formula (I) $0.03a < \Sigma cn < 0.5a$.
12. The method according to claim 1 wherein the compound of formula (I) is obtainable or is obtained by heating a starting material comprising a layered double hydroxide structure at a temperature of from 200° C. to 600° C.
13. The method according to claim 12 wherein the compound of formula (I) is obtainable or is obtained by heating a starting material comprising a layered double hydroxide structure at a temperature of from 250° C. to 500° C.
14. The method according to claim 12 wherein the starting material comprises a compound of formula (II):

$$M^{II}_{1-x}M^{III}_{x}(OH)_{2}A^{n-}_{y} \cdot mH_2O \quad (II)$$

wherein $M^{II}$ is the at least one divalent metal;
$M^{III}$ is the at least one trivalent metal;
$A^{n-}$ is at least one n-valent anion;

$x=\Sigma yn$;

$0<x\leq 0.4$;
$0<y\leq 1$; and
$0<m\leq 10$.

15. The method according to claim 1, wherein the mixed metal compound is provided in the form of a granular material, comprising:
   (i) at least 50% by weight, based on the weight of the granular material, of the mixed metal compound;
   (ii) from 3 to 12% by weight, based on the weight of the granular material, of non-chemically bound water; and
   (iii) no greater than 47% by weight, based on the weight of the granular material, of an excipient.
16. The method according to claim 15 wherein the mixed metal compound provided in the form of a granular material has less than 15% by weight crystallite-surface absorbed water.
17. The method according to claim 16 wherein the mixed metal compound has less than 10% by weight crystallite-surface absorbed water.
18. The method according to claim 16 wherein the mixed metal compound has less than 1% by weight crystallite-surface absorbed water.
19. The method according to claim 15 wherein the granular material comprises from 5 to 20% by weight of pregelatinised starch as excipient based on the weight of the granular material.
20. The method according to claim 15 wherein the granular material comprises from 1 to 15% by weight of cross linked polyvinylpyrrolidone as excipient based on the weight of the granular material.
21. The method according to claim 20 wherein the excipient comprises at least pregelatinised starch and cross linked polyvinylpyrrolidone.
22. The method according to claim 15 wherein at least 90% by weight of the granules of the granular material have a diameter less than 1180 micrometers.
23. The method according to claim 15 wherein the granular material is contained within a water resistant capsule.
24. The method according to claim 15 wherein a lubricant is provided between the granules.
25. The method according to claim 24 wherein the lubricant is or comprises magnesium stearate.
26. The method according to claim 15 wherein the granular material is coated with a water-resistant coating.

27. The method according to claim 26 wherein the water-resistant coating comprises at least 30% by weight of a butylated methacrylate copolymer.

28. The method according to claim 1 wherein the mixed metal compound is provided in a dosage unit containing the mixed metal compound in an amount of at least 200 mg.

29. The method according to claim 1 wherein the trivalent metal is at least iron (III).

30. The method according to claim 1 wherein the trivalent metal is iron (III).

31. The method according to claim 1 wherein the divalent metal is at least magnesium.

32. The method according to claim 1 wherein the divalent metal is magnesium.

33. The method according to claim 1, wherein
the mixed metal compound contains iron (III) and magnesium, and is provided in the form of a granular material comprising:
(i) at least 50% by weight, based on the weight of the granular material, of the mixed metal compound;
(ii) from 3 to 12% by weight, based on the weight of the granular material, of non-chemically bound water; and
(iii) no greater than 47% by weight, based on the weight of the granular material, of an excipient.

34. The method according to claim 1 wherein the mixed metal compound is of formula (I):

$$M^{II}_{1-a}M^{III}_{a}O_{b}A^{n-}_{c} \cdot zH_2O \qquad (I)$$

wherein $M^{II}$ is magnesium;
$M^{III}$ is iron (III);
$A^{n-}$ is at least one n-valent anion;

$$2+a=2b+\Sigma cn;$$

$\Sigma cn<0.9a$; and
z is 2 or less.

35. The method according to claim 1 wherein the mixed metal compound contains at least one of hydroxyl and carbonate anions.

36. A method for neutralizing or buffering stomach acid in a subject, comprising administering a therapeutically effective amount of a mixed metal compound to said subject, wherein the mixed metal compound contains at least one trivalent metal selected from the group consisting of iron (III) and aluminum and at least one divalent metal selected from the group consisting of magnesium, iron, zinc, calcium, lanthanum, and cerium,
wherein
(A) the mixed metal compound is of formula (I):

$$M^{II}_{1-a}M^{III}_{a}O_{b}A^{n-}_{c} \cdot zH_2O \qquad (I)$$

where $M^{II}$ is the at least one divalent metal;
$M^{III}$ is the at least one trivalent metal;
$A^{n-}$ is at least one n-valent anion;
$2+a=2b+\Sigma an$;
$\Sigma cn<0.9a$; and
z is 2 or less.

37. The method according to claim 1 wherein the condition or disease characterized by elevated levels of stomach acid is selected from the group consisting of peptic ulcers, heartburn, acid indigestion and acid reflux.

38. The method according to claim 37 wherein the condition or disease is peptic ulcers.

39. The method according to claim 36, wherein the mixed metal compound is provided in the form of a granular material comprising:
(i) at least 50% by weight, based on the weight of the granular material, of the mixed metal compound;
(ii) from 3 to 12% by weight, based on the weight of the granular material, of non-chemically bound water; and
(iii) no greater than 47% by weight, based on the weight of the granular material, of an excipient.

* * * * *